US012274562B2

(12) United States Patent
Ginestet et al.

(10) Patent No.: US 12,274,562 B2
(45) Date of Patent: Apr. 15, 2025

(54) RE-WEARABLE PHYSIOLOGICAL MONITORING DEVICE

(71) Applicant: OTSUKA PHARMACEUTICAL CO. LTD., Tokyo (JP)

(72) Inventors: Jacques Ginestet, Redwood City, CA (US); James Hutchison, Palo Alto, CA (US); Todd Schoenberger, Redwood City, CA (US); Jessica Szejer, Redwood City, CA (US); Iacopo Ferrari, Milan (IT)

(73) Assignee: OTSUKA PHARMACEUTICAL CO. LTD., Tokyo (JP)

( * ) Notice: Subject to any disclaimer, the term of this patent is extended or adjusted under 35 U.S.C. 154(b) by 1063 days.

(21) Appl. No.: 17/252,639

(22) PCT Filed: Jun. 14, 2019

(86) PCT No.: PCT/US2019/037382
§ 371 (c)(1),
(2) Date: Dec. 15, 2020

(87) PCT Pub. No.: WO2019/241753
PCT Pub. Date: Dec. 19, 2019

(65) Prior Publication Data
US 2021/0259634 A1    Aug. 26, 2021

Related U.S. Application Data

(60) Provisional application No. 62/685,784, filed on Jun. 15, 2018.

(51) Int. Cl.
*A61B 5/00*    (2006.01)
*A61B 5/307*   (2021.01)
*A61B 5/332*   (2021.01)

(52) U.S. Cl.
CPC .......... *A61B 5/6833* (2013.01); *A61B 5/0002* (2013.01); *A61B 2560/0214* (2013.01);
(Continued)

(58) Field of Classification Search
CPC .... A61B 2560/0214; A61B 2560/0285; A61B 2560/045; A61B 2560/0456;
(Continued)

(56) References Cited

U.S. PATENT DOCUMENTS

2003/0138610 A1* 7/2003 Tao ................... H05K 3/4664
                                                      428/209
2008/0228038 A1* 9/2008 McMahon ......... A61B 1/00114
                                                      600/223

(Continued)

FOREIGN PATENT DOCUMENTS

WO    2019241753 A1    12/2019

OTHER PUBLICATIONS

Written Opinion dated Jun. 30, 2022, issued in the corresponding Singapore Patent Application No. 11202012488Y, pp. 1-11.
(Continued)

*Primary Examiner* — Jonathan T Kuo
*Assistant Examiner* — Vynn V Huh
(74) *Attorney, Agent, or Firm* — Pillsbury Winthrop Shaw Pittman LLP

(57) ABSTRACT

A re-wearable physiological monitoring device includes a reusable component and a disposable component. The reusable component includes an electronics module and a latching system for latching the reusable component to the disposable component. The disposable component includes an adhesive patch to be adhered to a user's skin, two electrodes to receive electrical signals from the user's skin, a cradle for the reusable component to be latched on, and a battery to power the device. The disposable component may
(Continued)

include a "battery disconnect switch" for disconnecting the battery when the reusable component is not latched on; a gasket for isolating each contact between the reusable component and the disposable component in a waterproof enclosure; and a printed contact within the disposable component that is resistant to scratching. A latching system for the device may include two snap fasteners, alignment feet for keeping the reusable component aligned with the disposable component, and an asymmetrical wall to prevent the reusable component from being placed on the disposable component in the wrong orientation. A method of assembling the reusable component by ultrasonic welding is also disclosed.

10 Claims, 16 Drawing Sheets

(52) U.S. Cl.
CPC . *A61B 2560/0285* (2013.01); *A61B 2560/045* (2013.01); *A61B 2560/0456* (2013.01); *A61B 2562/164* (2013.01); *A61B 2562/227* (2013.01)

(58) Field of Classification Search
CPC ........ A61B 2562/164; A61B 2562/227; A61B 5/0002; A61B 5/6833
See application file for complete search history.

(56) References Cited

U.S. PATENT DOCUMENTS

| | | |
|---|---|---|
| 2014/0003166 A1 | 1/2014 | Kobata |
| 2014/0009467 A1 | 1/2014 | Akenine-Moller et al. |
| 2014/0031663 A1 | 1/2014 | Gallego et al. |
| 2014/0094676 A1 | 4/2014 | Gani et al. |
| 2014/0224652 A1* | 8/2014 | Gallardo .............. G01N 27/308 |
| | | 427/122 |
| 2014/0276167 A1* | 9/2014 | Dasgupta ............. A61B 5/7203 |
| | | 600/300 |
| 2015/0023809 A1 | 1/2015 | Yamada et al. |
| 2015/0087951 A1 | 3/2015 | Felix et al. |
| 2015/0238094 A1* | 8/2015 | Lai ....................... A61B 5/0006 |
| | | 600/509 |
| 2016/0120433 A1 | 5/2016 | Hughes et al. |
| 2017/0015092 A1 | 6/2017 | Kubota et al. |
| 2017/0150927 A1 | 6/2017 | Kubota et al. |
| 2018/0035909 A1 | 2/2018 | Hadley et al. |
| 2019/0274522 A1* | 9/2019 | Maiorano ........... A61B 1/00179 |

OTHER PUBLICATIONS

Search Report dated Jun. 8, 2022, issued in the corresponding Singapore Patent Application No. 11202012488Y, pp. 1-5.
International Search Report and Written Opinion for International PCT Application No. PCT/US2019/037382, dated Nov. 6, 2019.

* cited by examiner

RE-WEARABLE PHYSIOLOGICAL MONITORING DEVICE

CROSS REFERENCES TO RELATED APPLICATIONS

This application is related to U.S. Provisional Application No. 62/685,855, titled "MONITORING A SENSOR ASSEMBLY FOR REPLACEMENT STRIP," filed Jun. 15, 2018 and U.S. Provisional Application No. 62/685,878, titled "LOW POWER RECEIVER FOR IN VIVO CHANNEL SENSING AND INGESTIBLE SENSOR DETECTION WITH WANDERING FREQUENCY," filed Jun. 15, 2018, the entire contents of each of which are incorporated herein by reference in their entireties and for all purposes.

PRIORITY

This application is a U.S. National Stage Entry under 35 U.S.C. § 371 of International Patent Application No. PCT/US2019/037382, entitled RE-WEARABLE PHYSIOLOGICAL MONITORING DEVICE, which claims priority to U.S. Provisional Patent Application No. 62/685,784, titled RE-WEARABLE PHYSIOLOGICAL MONITORING DEVICE, filed Jun. 15, 2018, the entire disclosures of which are hereby incorporated by reference herein.

BACKGROUND

The present disclosure relates generally to physiological monitoring devices, and more specifically to physiological monitoring devices comprising a disposable component and a reusable component that are intended to be adhered to a user's skin.

Wearable physiological monitoring devices are becoming more and more widespread, and as they become more common, usability and convenience issues become more and more salient. Many users have to wear their physiological monitoring device for days, weeks, or even months or years, in a wide range of different environments, including environments that involve water (for example, showering or swimming). Some users of physiological monitoring devices have cognitive or executive-function issues that make it difficult for them to remember to maintain their physiological monitoring device—for example, by changing its battery—or to Figure out how to connect or disconnect different parts of the device. Other users may have motor-control issues that make it difficult to actually perform the actions necessary to connect or disconnect different parts of the device. Furthermore, most users, even those without any cognitive or motor-control issues, dislike it when a physiological monitoring device breaks and needs to be repaired.

All of these challenges apply particularly to an adhesive patch device comprising a reusable component and a disposable component. The user has to know how to connect the reusable component to the disposable component; the user has to enter environments involving water; the user has to change the device's battery and adhesive; and the user needs a reliable device that does not break.

A need exists for a durable, reliable, easy to use wearable physiological monitoring device that is safe to use around water and that is easy to maintain and easy to connect and disconnect.

SUMMARY

In some embodiments, a device of the present disclosure comprises a disposable component and a reusable component. The disposable component comprises two electrodes intended to make connection with a user's skin, and a cradle comprising a battery and electrical contacts connected to the battery and to the electrodes. The cradle also comprises a latching system for the reusable component to latch onto. The reusable component comprises an electrical interface to the cradle and a reusable component latching system configured to engage the disposable component latching system. In some embodiments, the cradle also comprises a battery disconnect switch connected between the first electrical contact and the battery, such that the battery disconnect switch disconnects the battery from the first electrical contact when no pressure is applied to the battery disconnect switch, and connects the battery to the first electrical contact when pressure is applied to the battery disconnect switch. In some embodiments, the reusable component comprises a protrusion configured in such a way as to apply pressure to the battery disconnect switch when the reusable component is latched to the cradle.

In some embodiments, the device of the present disclosure comprises a disposable component and a reusable component. The disposable component comprises two electrodes intended to make connection with a user's skin, and a cradle comprising a battery and electrical contacts connected to the battery and to the electrodes. The cradle also comprises a latching system for the reusable component to latch onto. The reusable component comprises an electrical interface to the cradle and a reusable component latching system configured to engage the disposable component latching system. In some embodiments, all the electrical connectors in the reusable component are spring loaded electrical connectors, and each one of the electrical contacts in the cradle comprise two layers of ink—a layer of a highly conductive first ink comprising large metal particles, and a layer of a second ink applied on top of the layer of first ink, wherein the second ink comprises carbon particles.

In some embodiments, the device comprises a plastic housing and a printed circuit board assembly (PCBA) located inside the plastic housing. The plastic housing comprises a top half and a bottom half. The PCBA is not rigidly attached to either the top half or the bottom half during assembly; instead, it is placed on the bottom half and then the top half is placed on top of the bottom half, and the ultrasonic weld is performed. The PCBA is not mechanically coupled to either the top half or the bottom half during the ultrasonic weld or at any other point.

In some embodiments, the device comprises a disposable component and a reusable component. The disposable component comprises two electrodes intended to make connection with a user's skin, and a cradle comprising a battery and electrical contacts connected to the battery and to the electrodes. The cradle also comprises a latching system for the reusable component to latch onto. The reusable component comprises an electrical interface to the cradle and a reusable component latching system configured to engage the disposable component latching system. In some embodiments, the device also comprises a gasket that provides an individual enclosure around each individual electrical contact, to prevent water from short-circuiting any two electrical contacts even if it is present around any given electrical contact.

In some embodiments, the device comprises a disposable component and a reusable component. The disposable component comprises two electrodes intended to make connection with a user's skin, and a cradle comprising a battery and electrical contacts connected to the battery and to the electrodes. The cradle also comprises a latching system for the reusable component to latch onto. The reusable component comprises an electrical interface to the cradle and a reusable component latching system configured to engage the disposable component latching system. In some embodiments, the device also comprises an asymmetrical wall feature in the reusable component latching system and an asymmetrical cradle feature in the disposable component latching system that is configured to engage with the asymmetrical wall feature in only one orientation of the reusable component with respect to the disposable component.

In some embodiments, the device comprises a disposable component and a reusable component. The disposable component comprises two electrodes intended to make connection with a user's skin, and a cradle comprising a battery and electrical contacts connected to the battery and to the electrodes. The cradle also comprises a latching system for the reusable component to latch onto. The reusable component comprises an electrical interface to the cradle and a reusable component latching system configured to engage the disposable component latching system. In some embodiments, the device also comprises at least two protrusions located around the perimeter of the reusable component and at least two cutouts located around the perimeter of the disposable component, wherein each one of the at least two protrusions engages with one of the at least two cutouts when the reusable component is placed on the disposable component.

In some embodiments, the device comprises a disposable component and a reusable component. The disposable component comprises two electrodes intended to make connection with a user's skin, and a cradle comprising a battery and electrical contacts connected to the battery and to the electrodes. The cradle also comprises a latching system for the reusable component to latch onto. The reusable component comprises an electrical interface to the cradle and a reusable component latching system configured to engage the disposable component latching system. In some embodiments, the device also comprises a front snap connector and a rear snap connector, such that the reusable component may be latched onto the disposable component regardless of angle of approach.

LIST OF FIGURES

DETAILED DESCRIPTION

Figure 1:
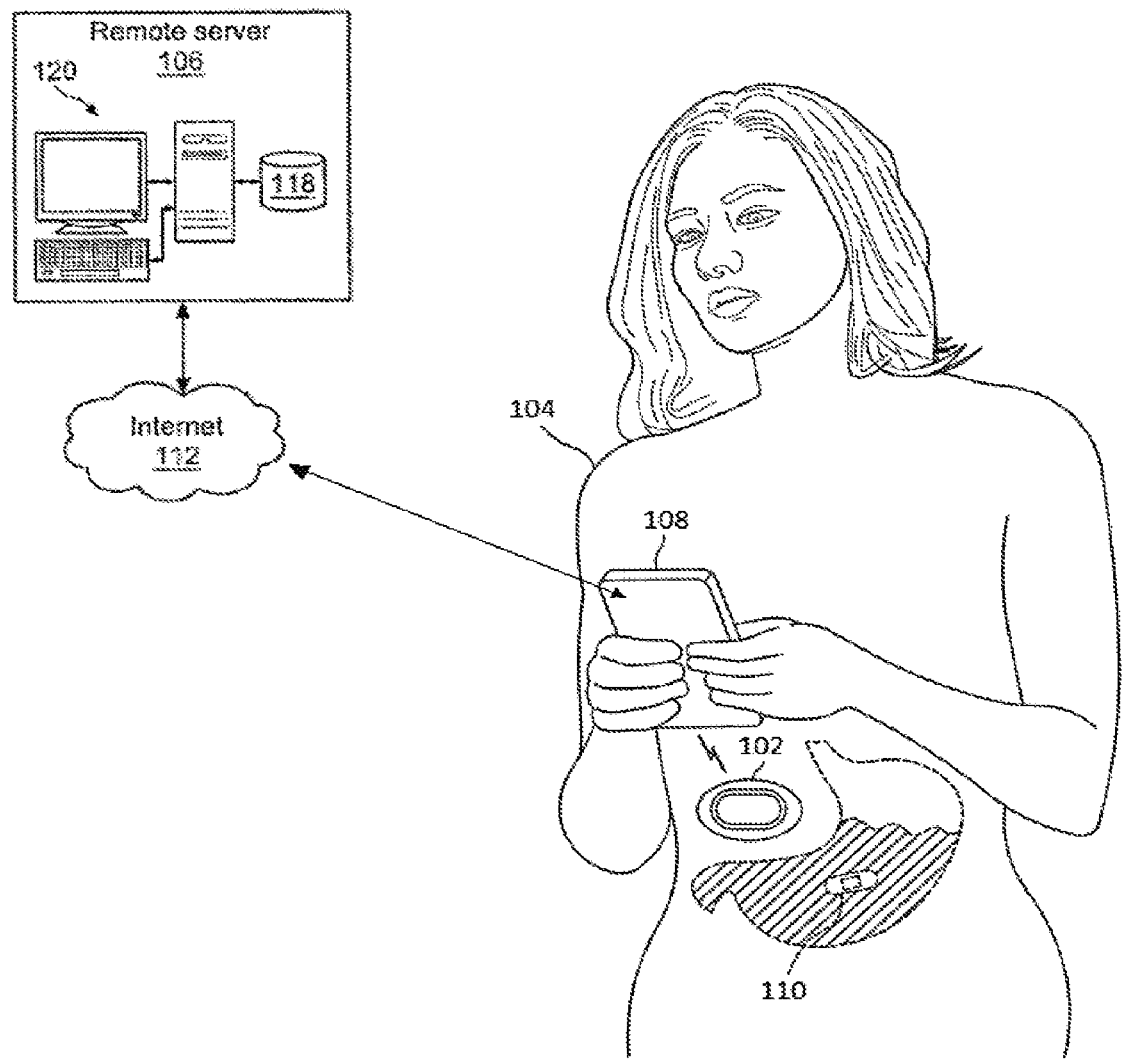
FIG. 1 shows a view of a re-wearable physiological monitoring device according to at least one aspect of the present disclosure.

An object of the present disclosure is to provide a re-wearable physiological monitoring device comprising a reusable component and a disposable component that is safe for use in or around water.

Another object of the present disclosure is to provide a re-wearable physiological monitoring device comprising a reusable component and a disposable component that requires minimal maintenance by the user.

Another object of the present disclosure is to provide a re-wearable physiological monitoring device comprising a reusable component and a disposable component that is easy to manufacture with a low defect rate.

Another object of the present disclosure is to provide a re-wearable physiological monitoring device comprising a reusable component and a disposable component that has reliable electrical connections between the reusable component and the disposable component.

Another object of the present disclosure is to provide a re-wearable physiological monitoring device comprising a reusable component and a disposable component, where the latch between the reusable component and the disposable component is easy for a user to connect and disconnect.

General Discussion of Re-Wearable Physiological Monitoring Device

Before explaining the various embodiments of the re-wearable physiological monitoring device in detail, it should be noted that the various embodiments disclosed herein are not limited in their application or use to the details of construction and arrangement of parts illustrated in the accompanying drawings and description. Rather, the disclosed embodiments are may be positioned or incorporated in other embodiments, variations and modifications thereof, and may be practiced or carried out in various ways. Accordingly, embodiments of the re-wearable physiological monitoring device disclosed herein are illustrative in nature and are not meant to limit the scope or application thereof. Furthermore, unless otherwise indicated, the terms and expressions employed herein have been chosen for the purpose of describing the embodiments for the convenience of the reader and are not to limit the scope thereof. In addition, it should be understood that any one or more of the disclosed embodiments, expressions of embodiments, and/or examples thereof, can be combined with any one or more of the other disclosed embodiments, expressions of embodiments, and/or examples thereof, without limitation.

In the following description, like reference characters designate like or corresponding parts throughout the several views. Also, in the following description, it is to be understood that terms such as front, back, inside, outside, top, bottom and the like are words of convenience and are not to be construed as limiting terms. Terminology used herein is not meant to be limiting insofar as devices described herein, or portions thereof, may be attached or utilized in other orientations. The various embodiments will be described in more detail with reference to the drawings.

The present disclosure is directed generally to various aspects of a re-wearable physiological monitoring device comprising a reusable component and a disposable component, wherein the re-wearable physiological monitoring device may be used for monitoring at least one physiological and/or physical parameter associated with the wearer of the re-wearable physiological monitoring device. The at least one monitored parameter may include, for example, a physiological and/or physical parameter associated with the subject. For example, the reusable component may be configured to monitor parameters, such as, without limitation, skin impedance, electro cardiogram signals, conductively transmitted current signal, position of wearer, temperature, heart rate, perspiration rate, humidity, altitude/pressure, global positioning system (GPS), proximity, bacteria levels, glucose level, chemical markers, blood oxygen levels, among other physiological and physical parameters. In an embodiment, the reusable component is configured to detect signals sent by an ingestible event marker (IEM) upon ingestion thereof by the wearer.

It will be appreciated that the term "medication" or "dose form" as used throughout this disclosure includes various forms of ingestible, inhalable, injectable, absorbable, or otherwise consumable medicaments and/or carriers therefor such as, for example, pills, capsules, gel caps, placebos, over capsulation carriers or vehicles, herbal, over-the-counter (OTC) substances, supplements, prescription-only medication, ingestible event markers (IEM), and the like.

In one aspect, shown in FIG. 1, the re-wearable physiological monitoring device 102 is removably attachable to a living subject 104, such as a person or other biological life form. In one aspect, the re-wearable physiological monitoring device 102 is configured to monitor at least one parameter. The at least one monitored parameter may include, for example, a physiological and/or physical parameter associated with the subject. For example, the re-wearable physiological monitoring device 102 may be configured to monitor parameters, such as, without limitation, skin impedance, electro cardiogram signals, conductively transmitted current signal, position of wearer, temperature, heart rate, perspiration rate, humidity, altitude/pressure, global positioning system (GPS), proximity, bacteria levels, glucose level, chemical markers, blood oxygen levels, among other physiological and physical parameters. In one aspect, the re-wearable physiological monitoring device 102 is configured to monitor the ingestion of an ingestible event marker 110.

In one aspect, the re-wearable physiological monitoring device 102 is wirelessly paired with a mobile device 108, such as a smartphone or a tablet. The wireless connection between the re-wearable physiological monitoring device 102 and the mobile device 108 may be Bluetooth, wi-fi, or any other short-range wireless connection. The re-wearable physiological monitoring device 102 may transmit the monitored parameters comprising physiological data and/or ingestion data to the mobile device 108.

In one aspect, the mobile device 108 is configured to wirelessly communicate the at least one monitored parameter over a communication network to a back-end or remote server or remote node 106. The communication network is preferably the Internet 112. The mobile device 108 may also send associated information along with the monitored parameter. The information associated with the monitored parameter(s) may include, for example, raw measurement data, processed data, and/or any combination thereof. The information also may include an identification number, patient identification information (e.g., name, address, phone number, email, social network web address), dosing unit identification, ingestible event marker system identification, time and date stamp when a dose form package is opened, time and date stamp when the ingestible event marker system was ingested by the patient and activated, among other information. A processing system 120 at the remote node 106 receives the information and stores it for processing by the database 118.

Still with reference to FIG. 1, the remote node 106 comprises a processing system 120 communicatively coupled to a database 118. Information associated with all subjects 104, e.g., patients, including identity and medication types and doses, may be stored in the database 118. The processing system 120 receives information from the mobile device 108 and accesses the information in the database 118 associated with the remote node 106 to provide information to the care provider through the re-wearable physiological monitoring device 102. The remote node 106 can communicate information including a photo of the patient for identification, the type of medication available to the care provider, as well as confirmation of the type and dose of medication that the care provider selects and delivers to the patient. The mobile device 108 can communicate with the remote node 106 using any mode and frequency of communication that is available in at the site, such as wireless, G2, G3, G4, real-time, periodically based on predetermined time delays, as well as store and forward at later time.

The processing system 120 at the remote node 106 may comprise servers configured as desired, e.g., to provide for subject directed permissions. For example, the servers may be configured to allow a family caregiver to participate in the subject's therapeutic regimen, e.g., via an interface (such as a web interface) that allows the family caregiver to monitor alerts and trends generated by the server, and provide support back to the patient. The servers also may be configured to provide responses directly to the subject, e.g., in the form of subject alerts, subject incentives, which are relayed to the subject via the communication device. The servers also may interact with a health care professional, e.g., RN, physician, which can use data processing algorithms to obtain measures of health and compliance of the subject, e.g., wellness index summaries, alerts, cross-patient benchmarks, and provide informed clinical communication and support back to the patient. The servers also may interact with pharmacies, nutrition centers, and drug manufactures.

In one aspect, the remote node 106 may store in the database 118 the time and date when a dose form was taken by the subject 104. In addition, when an event marker system is provided in the dosing unit, the time and date stamp of when the event marker system was ingested by the patient also may be stored in the database 118. In addition, an identification number such as a serial number, for example, identifying the single- or multi-dose packages, the type of package (single, multiple, morning, afternoon, evening, daily, weekly, monthly dosing event, and so on) the individual patient identification, the date of pre-packaging, the source, and the contents of the package, for example, may be stored in the database 118. In some aspects, the expiration date or shelf life of one or all of the medication(s) or dose forms also may be stored in the database 118.

The chipset in the re-wearable physiological monitoring device 102 provides two-way data communication between the re-wearable physiological monitoring device 102 and the mobile device 108. In one aspect, when the subject 104 ingests a dose form comprising an event indicator system 110, the event indicator system communicates with the re-wearable physiological monitoring device 102, which includes various electronic modules for receiving a unique signature from the event indicator system and communicating with the mobile device 108.

In other aspects, the re-wearable physiological monitoring device 102 can be triggered to initiate a data transmission to the mobile device 108 based on a variety of triggers. These triggers include, without limitation, a timer, real time clock, an event, detection of ingestion of an event marker system, detection of a particular code received from the event marker system, receipt of a particular monitored parameter or value of such monitored parameter, receipt of trigger data from the mobile device 108, among others.

Figure 2:
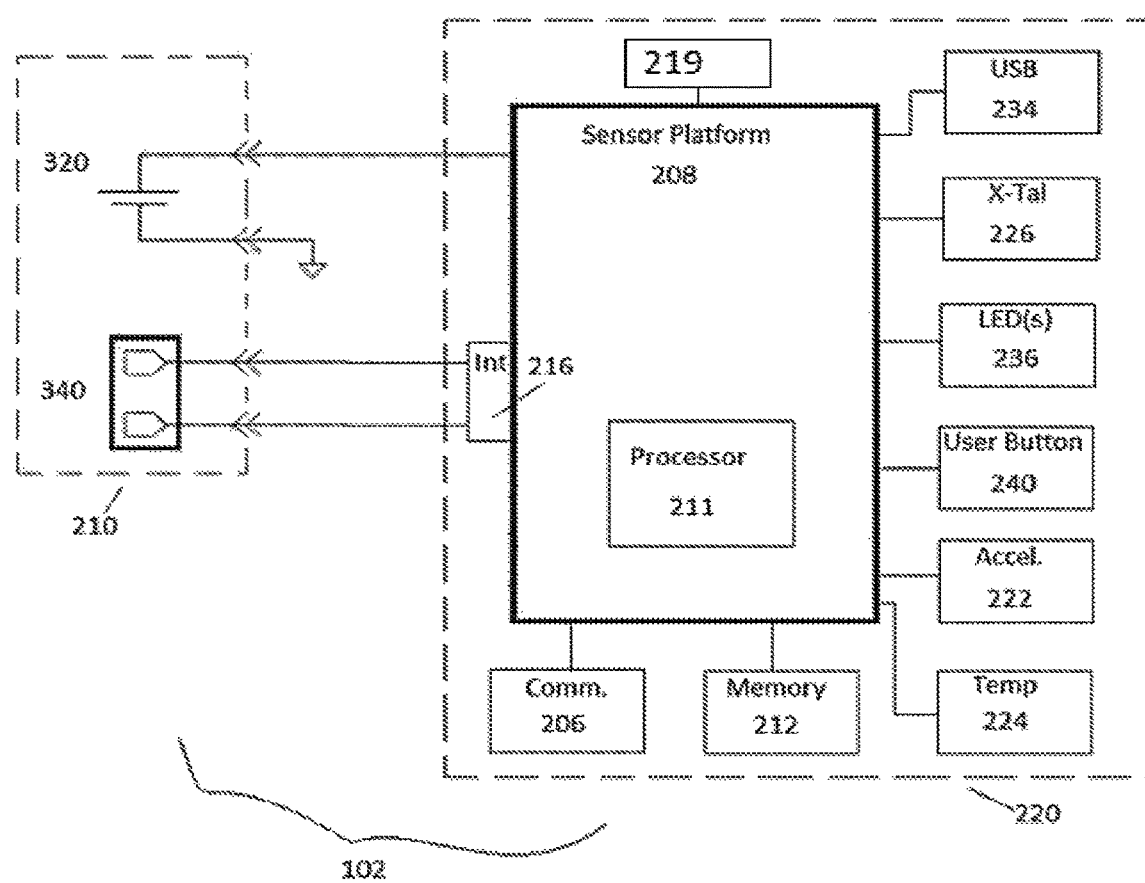
FIG. 2 shows a block diagram of a re-wearable physiological monitoring device according to at least one aspect of the present disclosure.

FIG. 2 is a system diagram of one aspect of the re-wearable wireless device 102. In one aspect, the re-wearable wireless device 102 is a two-piece device comprising a disposable component 210 and a reusable component 220. The reusable component 220 comprises an electronics module. The electronics module of the reusable component 220 comprises a wireless communication circuit 206, such as a mobile chipset RF wireless circuit or simply cellular radio. The electronics module of the reusable component 220 comprises an ASIC-based sensor platform 208 that includes a hardware architecture and software framework to implement various aspects of the re-wearable wireless device 102. In one aspect, the ASIC-based sensor platform 208 may be disposed on and interfaced with a printed circuit board assembly (PCBA). The wireless communication circuit 206 may be a low power mobile chipset and is configured to connect to the cellular network 108 as well as other wireless devices (cell-phones, smart phones, tablet computers, laptop computers, gateway devices, among others). The disposable component 210 interfaces with the PCBA and the first electronic module 220. In one aspect, the electronic module 220 and the disposable component 210 each may comprise additional modules that reside on or off the PCBA or, in another aspect may be disposed on the PCBA.

In one aspect, the reusable electronic module 220 provides a sensor platform and comprises circuits designed to interface with different sensors and comprises various combinations of the following components. In various aspects, the reusable electronic module 220 ASIC-based sensor platform provides a combination of analog front-end, vector/digital signal processing, microprocessor and memory in a single low-power ASIC/chip that comprises an "ASIC-based sensor platform" 208 with multiple functions: software-defined radio for detection of ingestible event markers, sensing and decoding of ECG, AC skin impedance measurements, temperature measurements, DC skin impedance (e.g., GSR) measurements and other biological/medical data sensors.

In one aspect, the reusable electronic module 220 comprises an ASIC sensor platform 208, a controller or processor 211, e.g., a microcontroller unit (MCU), a radio frequency (RF) wireless comm circuit 206, among other components described hereinbelow.

In one aspect, the ASIC portion 208 of the reusable electronic module 220 may comprise a core processor 211 such as, for example, an ARM Cortex™ M3 processor, for real-time applications, a signal processing accelerator such as, for example, a Vector Math Accelerator, program memory, data memory, serial interfaces such as, for example, SPI, universal asynchronous receiver transmitter (UART), two-wire multi-master serial single ended bus interface (12C), general purpose input/output (GPIO), a real-time clock, an analog-to-digital converter (ADC), gain and conditioning circuits for bio-potential signals, light emitting diode (LED) drivers, among other components. The reusable electronic module 220 also comprises a connection port to external memory, a connection port to external sensors, and a hardware accelerator. The processor 211 receives a signal from each of the sensors by operating the analog front end for analog sensors and by receiving digital data from sensors with the ADC digitizer. The processor 211 then processes the data and stores the results into the memory 212 in form of data records. In one aspect, the processor 211 may have a very long instruction word (VLIW) processor architecture.

In one aspect, the reusable electronic module 220 also comprises a universal serial bus 234 (USB), an accelerometer 222, memory 212, one or more LEDs 236, a 32 KHz crystal 226, a user button 240 that may be used to initiate a communication connection with an external device, sensor interfaces 216. In other aspects, the reusable electronic module 220 may comprise a gyroscope, and circuits for processing ECG, temperature, and accelerometer signals. In other aspects, the reusable electronic module 220 also may comprise body composition and $SpO_2$ pulse oximetry circuits that monitor functional oxygen saturation of arterial blood by calculating the ratio of oxygenated hemoglobin to hemoglobin that is capable of transporting oxygen. An SpO2 pulse oximetry circuit may be configured to provide continuous, noninvasive measurements of SpO2 and, in one aspect, can display a plethysmographic waveform. Heart rate values are may be derived from the pulse oximetry signal.

In one aspect, the reusable electronic module 220 comprises an RF wireless communication circuit 206. The RF wireless communication circuit 206 comprises an antenna for receive and transmit wireless signals, a transmitter circuit, a receiver circuit, and a link master controller that includes a mechanism to connect (establish a link) to another, external, wireless device and transfer data, as described in more detail hereinbelow. In one aspect, the link master controller establishes connection to an external device such as a mobile device 108. As a master of the link, the link master controller performs control of data transmission over the link to the external device, including timing control and radio frequency control (channel hopping). The link master controller sends a signal to the external device with an instruction that gives number of data records stored in memory (a total number of all data records and a total number of records of each data type). In various aspects, the RF wireless communication circuit 206 may be implemented using a mobile chipset available from a variety of vendors including, without limitation Tegra by Nvidia, Snapdragon by Qualcomm, OMAP by Texas Instruments, Exynos by Samsung, Ax by Apple, NovaThor by ST-Ericsson, Atom by Intel, i.MX by Freescale Semiconductor, RK3xxx by Rockchip, A31 by AllWinner, among others. Such mobile chipsets are employed by mobile telephones, otherwise known in the art as "mobile," "wireless," "cellular phone," "cell phone," "hand phone (HP)," "smart phone," among others.

After each connection, the processor 211 continues to receive all sensor signals, processes the data and stores new data records into the memory 212. Upon each subsequent connection link master controller sends a signal to an external device with new data records since last connection and confirms that records were transmitted successfully. The link master controller receives a signal from the external device that establishes if the external device is ready to receive data records and also receives a signal from the external device that establishes which data records were not transferred successfully. The link master controller avoids repeating the transmission of the data records that already have been transmitted, which improves battery 320 power use for a longer operation and resends all data records that were not transferred successfully. The link master controller may delete from the memory all or some successfully transferred data records at a later time (for example, when the memory 212 gets full).

In one aspect, the reusable electronic module 220 comprises a sensor interface 216 between electrodes 340 and one or more band pass filters or channels. The sensor interface 216 provides an analog front end and may include programmable gain or fixed gain amplifiers, programmable low-pass filter, programmable high-pass filter. The sensor interface 216 may comprise active signal conditioning circuits including strain gauge measurement circuits, for example. One channel receives low frequency information associated with the physiological data of the subject (e.g., user) and the other channel receives high frequency information associated with an electronic device within the subject. In one alternative aspect, an additional channel is provided for receiving DC data of the subject. The high frequency information is passed to a digital signal processor (DSP) implemented in the ASIC portion 208 and then to a processor 211 (e.g., a control processor) portion of the re-wearable wireless device 102 for decompression and decoding. The low frequency information is either passed to the DSP portion of the ASIC portion 208 and then to processor 211, or passed directly to the processor 211. The DC information is passed directly to the processor 211. The DSP portion of the ASIC portion 208 and the processor 211 decode the high frequency, low frequency and DC information or data. This information is then processed and prepared for transmission.

In one aspect, signal processing may or may not be applied to the raw data collected. Signal processing may occur in the real space, complex number space, or in the polar coordinates space. Functions include filters, e.g., finite impulse response (FIR) and infinite impulse response (IIR), mixers, fats Fourier transforms (FFTs), cordics, and others. Raw data may simply be stored and processed downstream. The signal processing may occur in the processor (e.g., ARM Cortex™ M3) or may occur in the signal processing accelerator which is incorporated into the ASIC portion 208.

In one aspect, the reusable electronic module 220 comprises an accelerometer 222 and one or more temperature sensors 224. In one aspect, two temperature sensors are provided that are identical but placed in different locations— one close to the skin, another close to the ambient for measuring additional data. The temperature sensors 224 may be configured to measure and record, skin, ambient, and circuit board temperature. The temperature sensors 224 may be used to measure heat flux between the skin and the ambient temperature sensor. In one aspect, the temperature sensor 224 or sensors are thermistor devices with negative temperature coefficient (NTC) or positive temperature coefficient (PTC), and in another aspect temperature sensor 224 or sensors are using integrated semiconductor devices. This information is provided to the processor 211 and can be processed by the processor 211 and prepared for transmission by a transmitter portion of the RF wireless communication circuit 206. The physiological information measured is processed by the processor 211 and may be transmitted as real-time or raw data, or derived quantities or parameters may be transmitted.

In one aspect, the accelerometer 222 may be a 3-axis accelerometer with a resampling frequency correction processor. Digital accelerometer 222 sensors usually include a MEMS-based acceleration sensor element, a digitizer, and digital interface control logic. Typically these accelerometers use resistor-capacitor (RC) oscillator with low accuracy to strobe the digitizer sampling input. In order to employ signals from such accelerometer 222 in signal processing algorithms the accuracy of RC oscillators is not sufficient. Accordingly, in one aspect, the reusable electronic module 220 comprises an accelerometer sampling frequency correction processor that takes signals from the accelerometer 222 and performs re-sampling to compensate for the RC oscillator error.

In one aspect, the accelerometer 222 sampling frequency correction processor comprises a reference clock (high accuracy oscillator), a fixed up-sample block, a digital filter, a programmable down-sample block, and a control circuit that selects down-sample coefficient based on comparison of timing of the signal from accelerometer and the reference clock. The resampling function keeps alignment to a reference clock in a sliding window to generate a precise sampling rate. An algorithm calibrates the real time 32 kHz clock (X-Tal) 226. The accelerometer 222 sampling frequency correction processor sets the down-sampling coefficient for each frame of data from the accelerometer signal. The present approach provides tracking the timing of the accelerometer signal continuously and selecting the down-sampling coefficient to minimize the accumulated timing error. That allows continuous accelerometer 222 digital data to align to the accurate clock with high precision.

In one aspect, the reusable electronic module 220 employs a low-power low-memory data storage and transfer scheme. In one aspect, storage and transfer of data in the re-wearable wireless device 102 memory 212 is optimized for low-power and low memory usage. Sensor data is stored as records in the memory 212, each with a type identifier. Records are transferred in a packet payload to an external mobile device 108 by the RF wireless communication circuit 206. Records are stored sequentially with variable length to optimize space usage. A data directory is included which allows fast record read access from the memory 212. A data directory is included which allows fast counting of the data records by type.

In one aspect, the reusable electronic module 220 employs a high-assurance integrity data storage and transfer scheme. The re-wearable wireless device 102 memory storage and transfer scheme is designed for high-assurance data integrity. For each data record stored in the memory 212 of the re-wearable wireless device 102, there is an error-detecting code that can be used to detect data record corruption. When the re-wearable wireless device 102 reads a data record from the memory 212 prior to data packet transfer to the external device, the error-detecting code is checked. When the re-wearable wireless device 102 detects corruption of the stored data record, an error signal is sent to an external device by the RF wireless communication circuit 206. Each packet transferred from the re-wearable wireless device 102 to the external device contains an error-detecting code which can be used by the external device to detect packet corruption.

In one aspect, the signal processing accelerator portion of the ASIC portion 208 includes a computational engine optimized for implementing high efficiency signal processing tasks. In one implementation, signal processing functions are hard coded in logic. Such implementations may be 10× or more efficient compared to software-based algorithms implemented in software running on a processor 211 or microcontroller unit. The efficiency may be in chip sized, power consumption, or clock speed or some combination of all three. Another implementation maintains some level of programmability, but utilizes execution unit(s) that are optimized calculations. One example is an FFT-butterfly engine. The engine may enable FFT calculations for various size data sets, but maintain significant efficiency improvement over software running on a processor 211. The execution units also may be multiply accumulate units (MAC), which are a common DSP function block or could be a floating point calculation unit(s) or FIR filter primitives, etc. In these cases the efficiency for a given integrated circuit process is greater than that of software on a processor 211, but less than that of dedicated hardware, however they are much more flexible.

The signal processing accelerator maintains an interface between the processor 211. This interface may include first-in-first-out (FIFO) registers, dual port memories, the direct memory access (DMA) engine of the processor 211, and/or registers. The interface typically includes some form of contention recognition or avoidance which may be handled at the register-level or at the memory block level. Mechanisms involved may include register flags set, which can be polled by the processor 211 and signal processing accelerator, interrupts to signal either block or delay functions that hold a read or write request until the higher priority device has completed their activity.

In one aspect, the disposable component 210 is coupled to the reusable electronic module 220 on the PCBA with one or more sensors attached for interface to the item to be monitored (person, animal, machine, building, etc.). In one aspect, the disposable component 210 may comprise a battery 320, a cradle to hold the battery, battery holder or housing (covering) and one or more sensors, including but not limited to ambient and body temperature (temp) (living or not), ECG, GSR/electro-dermal activation (EDA), body composition (50 Hz), SpO2/pulse oximetry, strain gauge, among others. Various algorithms executed by the ASIC portion 208 or the processor 211 provide heat flux, HR, HRV, respiration, stress, ECG, steps, body angle, fall detection, among others.

The re-wearable wireless device 102 collects data from various sensors, applies signal processing algorithms to the data collected, stores the resulting information in memory, and forwards data/information to another device using either a wireless or wired connection. The user interface consists of one or two LEDs 236 and a push-button 240.

Power is provided from a primary battery 320. The battery is located in the disposable component 211 as shown. The battery 320 is preferably a disposable coin cell with a battery life approximately equal to the useful life of the adhesive strip of the disposable component, discussed hereinbelow.

The disposable component 210 may include electrodes 340 and one or more types of adhesives for adhering the re-wearable wireless device 102 to the skin of the subject 104 (FIG. 1), which has a typical life of about 3 to about 10 days on most people. The sensor data may include ECG data (via hydrogel electrodes) 340, accelerometer data in up to 3 axis, temperature data, adjacent to skin (thermistor), ambient (or case temperature away from body) (thermistor), temperature on the PCBA (silicon device incorporated into the ASIC portion 208), GSR, EDA (discrete stainless-steel electrodes), high-frequency, in-body electric signals—10 KHz and higher, sampled via conduction through the hydrogel skin electrodes (same as ECG).

As shown, the re-wearable wireless device 102 may comprise a memory 212. In various aspects, the memory 212 may comprise any machine-readable or computer-readable media capable of storing data, including both volatile and non-volatile memory. For example, memory may include read-only memory (ROM), random-access memory (RAM), dynamic RAM (DRAM), Double-Data-Rate DRAM (DDR-RAM), synchronous DRAM (SDRAM), static RAM (SRAM), programmable ROM (PROM), erasable programmable ROM (EPROM), electrically erasable programmable ROM (EEPROM), flash memory (e.g., NOR or NAND flash memory), content addressable memory (CAM), polymer memory (e.g., ferroelectric polymer memory), phase-change memory (e.g., ovonic memory), ferroelectric memory, silicon-oxide-nitride-oxide-silicon (SONOS) memory, disk memory (e.g., floppy disk, hard drive, optical disk, magnetic disk), or card (e.g., magnetic card, optical card), or any other type of media suitable for storing information.

The re-wearable wireless device 102 may comprise a processor 211 such as a central processing unit (CPU). In various aspects, the processor 211 may be implemented as a general purpose processor, a chip multiprocessor (CMP), a dedicated processor, an embedded processor, a digital signal processor (DSP), a network processor, a media processor, an input/output (I/O) processor, a media access control (MAC) processor, a radio baseband processor, a co-processor, a microprocessor such as a complex instruction set computer (CISC) microprocessor, a reduced instruction set computing (RISC) microprocessor, and/or a very long instruction word (VLIW) microprocessor, or other processing device. The processor also may be implemented by a controller, a microcontroller, an application specific integrated circuit (ASIC), a field programmable gate array (FPGA), a programmable logic device (PLD), and so forth.

In various aspects, the processor 211 may be arranged to run an operating system (OS) and various mobile applications. Examples of an OS include, for example, operating systems generally known under the trade name of Microsoft Windows OS, and any other proprietary or open source OS. Examples of mobile applications include, for example, a telephone application, a camera (e.g., digital camera, video camera) application, a browser application, a multimedia player application, a gaming application, a messaging application (e.g., e-mail, short message, multimedia), a viewer application, and so forth.

In various aspects, the processor 211 may be arranged to receive information through a communications interface. The communications interface may comprise any suitable hardware, software, or combination of hardware and software that is capable of coupling the re-wearable wireless device 102 to one or more networks and/or devices.

Wireless communication modes include any mode of communication between points that utilizes, at least in part, wireless technology including various protocols and combinations of protocols associated with wireless transmission, data, and devices. The points include, for example, wireless devices such as wireless headsets, audio and multimedia devices and equipment, such as audio players and multimedia players, telephones, including mobile telephones and cordless telephones, and computers and computer-related devices and components, such as printers.

Wired communication modes include any mode of communication between points that utilizes wired technology including various protocols and combinations of protocols associated with wired transmission, data, and devices. The points include, for example, devices such as audio and multimedia devices and equipment, such as audio players and multimedia players, telephones, including mobile telephones and cordless telephones, and computers and computer-related devices and components, such as printers.

In various aspects, the communications interface may comprise one or more interfaces such as, for example, a wireless communications interface, a wired communications interface, a network interface, a transmit interface, a receive interface, a media interface, a system interface, a component interface, a switching interface, a chip interface, a controller, and so forth. When implemented by a wireless device or within wireless system, for example, the local node 106 may include a wireless interface comprising one or more antennas, transmitters, receivers, transceivers, amplifiers, filters, control logic, and so forth.

In various aspects, the re-wearable wireless device 102 may provide voice and/or data communications functionality in accordance with different types of cellular radiotelephone systems. In various implementations, the described aspects may communicate over wireless shared media in accordance with a number of wireless protocols. Examples of wireless protocols may include various wireless local area network (WLAN) protocols, including the Institute of Electrical and Electronics Engineers (IEEE) 802.xx series of protocols, such as IEEE 802.11a/b/g/n, IEEE 802.16, IEEE 802.20, and so forth. Other examples of wireless protocols may include various wireless wide area network (WWAN) protocols, such as GSM cellular radiotelephone system protocols with GPRS, CDMA cellular radiotelephone communication systems with 1xRTT, EDGE systems, EV-DO systems, EV-DV systems, HSDPA systems, and so forth. Further examples of wireless protocols may include wireless personal area network (PAN) protocols, such as an Infrared protocol, a protocol from the Bluetooth Special Interest Group (SIG) series of protocols, including Bluetooth Specification versions v1.0, v1.1, v1.2, v2.0, v2.0 with Enhanced Data Rate (EDR), as well as one or more Bluetooth Profiles, and so forth. Yet another example of wireless protocols may include near-field communication techniques and protocols, such as electro-magnetic induction (EMI) techniques. An example of EMI techniques may include passive or active radio-frequency identification (RFID) protocols and devices. Other suitable protocols may include Ultra Wide Band (UWB), Digital Office (DO), Digital Home, Trusted Platform Module (TPM), ZigBee, and so forth.

Further, in various aspects, the re-wearable wireless device 102 may incorporate and/or be associated with, e.g., communicate with, various devices. Such devices may generate, receive, and/or communicate data, e.g., physiologic data. The devices include, for example, smartphones, tablets, "intelligent" devices such as gaming devices, e.g., electronic slot machines, handheld electronic games, electronic components associated with games and recreational activities.

Some embodiments may be implemented, for example, using a machine-readable medium or article which may store an instruction or a set of instructions that, if executed by a machine, may cause the machine to perform a method and/or operations in accordance with the embodiments.

Such a machine may include, for example, any suitable processing platform, computing platform, computing device, processing device, computing system, processing system, computer, processor, or the like, and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, and the like. The instructions may be implemented using any suitable high-level, low-level, object-oriented, visual, compiled and/or interpreted programming language, such as C, C++, Java, BASIC, Perl, Matlab, Pascal, Visual BASIC, assembly language, machine code, and so forth.

In various aspects, the re-wearable wireless device 102 also functions to communicate, e.g., receive and transmit, non-physiologic data. Example of non-physiologic data include, for example, gaming rules and data generated by a separate cardiac-related device such as an implanted pacemaker and communicated to the hub directly or indirectly.

Figure 3:
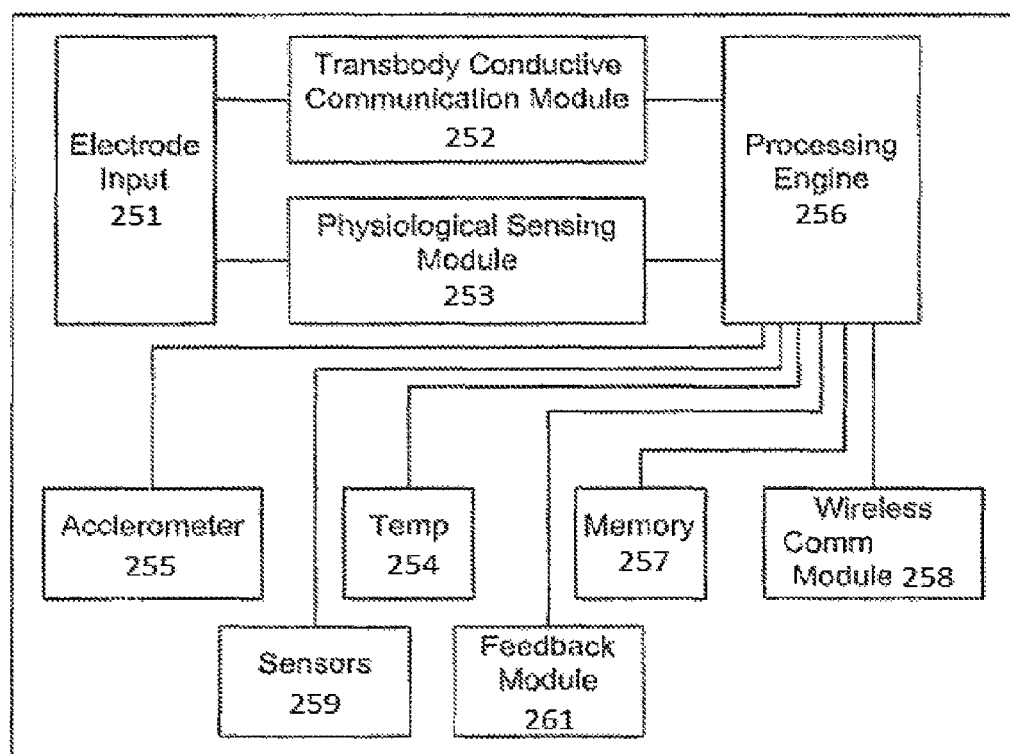
FIG. 3 shows a block diagram of a reusable component according to at least one aspect of the present disclosure.

FIG. 3 is a block functional diagram of one aspect of an integrated circuit component of the electronics module of the reusable component 220 of the re-wearable wireless device 102 shown in FIGS. 1 and 2. In FIG. 3, the electronics module of the reusable component 220 of the re-wearable wireless device 102 comprises an electrode input. Electrically coupled to the electrode input 251 are a transbody conductive communication module 252 and a physiological sensing module 253. In one aspect, the transbody conductive communication module 252 is implemented as a first, e.g., high, frequency (HF) signal chain and the physiological sensing module 253 is implemented as a second, e.g., low, frequency (LF) signal chain. Also shown are CMOS temperature sensing module 254 (for detecting ambient temperature) and a 3-axis accelerometer 255. The re-wearable wireless device 102 also comprises a processing engine 256 (for example, a microcontroller and digital signal processor), a non-volatile memory 257 (for data storage), and a wireless communication module 258 comprising a mobile chipset to receive and/or transmit data to and from a cellular communication network. In various aspects, the communication modules 252, 258 may comprise one or more transmitters/receivers ("transceiver") modules. As used herein, the term "transceiver" may be used in a very general sense to include a transmitter, a receiver, or a combination of both, without limitation. In one aspect, the transbody conductive communication module 252 is configured to communicate with an event marker system 110.

The sensors 259 typically contact the subject 104 (FIG. 1), e.g., are removably attached to the torso. In various aspects, the sensors 269 may be removably or permanently attached to the re-wearable wireless device 102. For example, the sensors 259 may be removably connected to the re-wearable wireless device 102 by snapping metal studs. The sensors 259 may comprise, for example, various devices capable of sensing or receiving the physiologic data.

The types of sensors 259 include, for example, electrodes such as biocompatible electrodes. The sensors 259 may be configured, for example, as a pressure sensor, a motion sensor, an accelerometer, an electromyography (EMG) sensor, an event marker system, a biopotential sensor, an electrocardiogram sensor, a temperature sensor, a tactile event marker sensor, and an impedance sensor.

The feedback module 261 may be implemented with software, hardware, circuitry, various devices, and combinations thereof. The function of the feedback module 261 is to provide communication with the subject 104 (FIG. 1) in a discreet, tactful, circumspect manner as described above. In various aspects the feedback module 261 may be implemented to communicate with the subject 104 using techniques that employ visual, audio, vibratory/tactile, olfactory, and taste.

Figure 4:
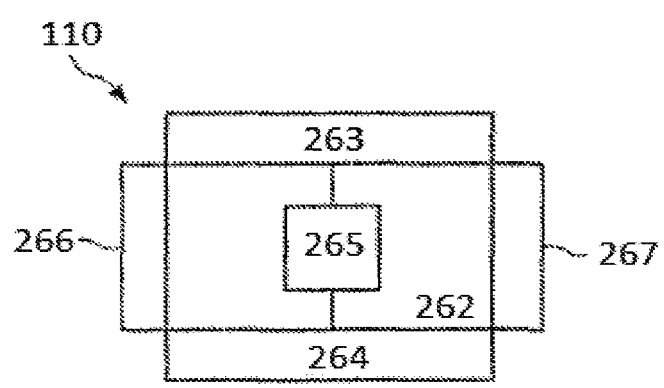
FIG. 4 shows a block diagram of an ingestible event marker system according to at least one aspect of the present disclosure.

FIG. 4 shows one aspect of an event marker system 110. In various aspects the event marker system 110 can be used in association with any medication product, as mentioned above, to determine the origin of the medication and to confirm that at least one of the right type and the right dosage of medication was delivered to the patient and in some aspects to determine when a patient takes the medication product. The scope of the present disclosure, however, is not limited by the environment and the medication product that may be used with the system 110. For example, the system 110 may be activated either in wireless mode, in galvanic mode by placing the system 110 within a capsule and then placing the capsule within a conducting fluid, or a combination thereof, or exposing the system 110 to air. Once placed in a conducting fluid, for example, the capsule would dissolve over a period of time and release the system 110 into the conducting fluid. Thus, in one aspect, the capsule would contain the system 110 and no product. Such a capsule may then be used in any environment where a conducting fluid is present and with any product. For example, the capsule may be dropped into a container filled with jet fuel, salt water, tomato sauce, motor oil, or any similar product. Additionally, the capsule containing the system 110 may be ingested at the same time that any pharmaceutical product is ingested in order to record the occurrence of the event, such as when the product was taken.

In the specific example of the system 110 combined with a medication or pharmaceutical product, as the product or pill is ingested, or exposed to air, the system 110 is activated in galvanic mode. The system 110 controls conductance to produce a unique current signature that is detected by the re-wearable wireless device 102, for example, thereby signifying that the pharmaceutical product has been taken. When activated in wireless mode, the system controls modulation of capacitive plates to produce a unique voltage signature associated with the system 110 that is detected.

In one aspect, the system 110 includes a framework 262. The framework 262 is a chassis for the system 110 and multiple components are attached to, deposited upon, or secured to the framework 262. In this aspect of the system 110, a digestible material 263 is physically associated with the framework 262. The material 263 may be chemically deposited on, evaporated onto, secured to, or built-up on the framework all of which may be referred to herein as "deposit" with respect to the framework 262. The material 263 is deposited on one side of the framework 262. The materials of interest that can be used as material 263 include, but are not limited to: Cu, CuCl, or CuI. The material 263 is deposited by physical vapor deposition, electrodeposition, or plasma deposition, among other protocols. The material 263 may be from about 0.05 to about 500 µm thick, such as from about 5 to about 100 µm thick. The shape is controlled by shadow mask deposition, or photolithography and etching. Additionally, even though only one region is shown for depositing the material, each system 110 may contain two or more electrically unique regions where the material 263 may be deposited, as desired.

Figure 7:
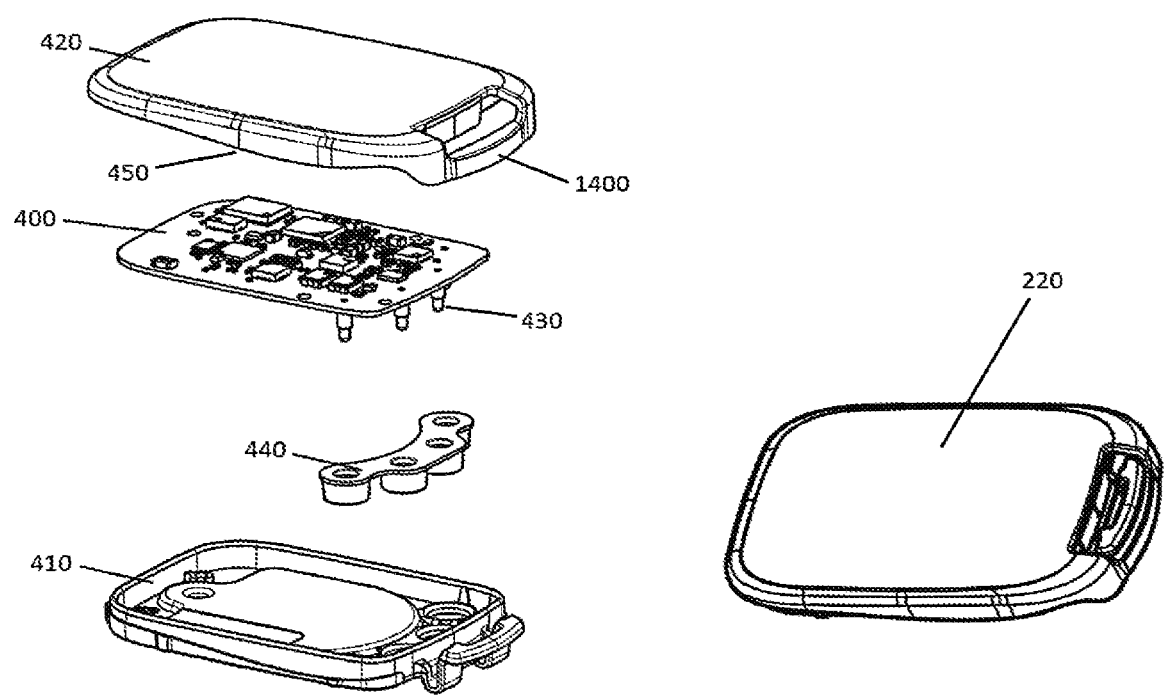
FIG. 7 shows two views of a reusable component according to at least one aspect of the present disclosure.

At a different side, which is the opposite side as shown in FIG. 7, another digestible material 264 is deposited, such that the materials 263, 264 are dissimilar and insulated from each other. Although not shown, the different side selected may be the side next to the side selected for the material 263. The scope of the present disclosure is not limited by the side selected and the term "different side" can mean any of the multiple sides that are different from the first selected side. In various aspects, the dissimilar material may be located at different positions on a same side. Furthermore, although the shape of the system is shown as a square, the shape may be any geometrically suitable shape. The materials 263, 264 are selected such that they produce a voltage potential difference when the system 110 is in contact with conducting liquid, such as body fluids. The materials of interest for material 264 include, but are not limited to: Mg, Zn, or other electronegative metals. As indicated above with respect to the material 263, the material 264 may be chemically deposited on, evaporated onto, secured to, or built-up on the framework. Also, an adhesion layer may be necessary to help the material 264 (as well as material 724 when needed) to adhere to the framework 722. Typical adhesion layers for the material 264 are Ti, TiW, Cr or similar material. Anode material and the adhesion layer may be deposited by physical vapor deposition, electrodeposition or plasma deposition. The material 264 may be from about 0.05 to about 500 µm thick, such as from about 5 to about 100 µm thick. However, the scope of the present disclosure is not limited by the thickness of any of the materials nor by the type of process used to deposit or secure the materials to the framework 262.

According to the disclosure set forth, the materials 263, 264 can be any pair of materials with different electrochemical potentials. Additionally, in the embodiments wherein the system 110 is used in-vivo, the materials 263, 264 may be vitamins that can be absorbed. More specifically, the materials 263, 264 can be made of any two materials appropriate for the environment in which the system 110 will be operating. For example, when used with an ingestible product, the materials 263, 264 are any pair of materials with different electrochemical potentials that are ingestible. An illustrative example includes the instance when the system 110 is in contact with an ionic solution, such as stomach acids. Suitable materials are not restricted to metals, and in certain embodiments the paired materials are chosen from metals and non-metals, e.g., a pair made up of a metal (such as Mg) and a salt (such as CuCl or CuI). With respect to the active electrode materials, any pairing of substances—metals, salts, or intercalation compounds—with suitably different electrochemical potentials (voltage) and low interfacial resistance are suitable.

Materials and pairings of interest include, but are not limited to, those reported in TABLE 1 below. In some embodiments, one or both of the metals may be doped with a non-metal, e.g., to enhance the voltage potential created between the materials as they come into contact with a conducting liquid. Non-metals that may be used as doping agents in certain embodiments include, but are not limited to: sulfur, iodine, and the like. In other cases, the materials are copper iodine (CuI) as the anode and magnesium (Mg)

as the cathode. Aspects of the present disclosure use electrode materials that are not harmful to the human body.

TABLE 1

|  | Anode | Cathode |
|---|---|---|
| Metals | Magnesium, Zinc Sodium (†), Lithium (†) Iron | |
| Salts | | Copper salts: iodide, chloride, bromide, sulfate, formate, (other anions possible) $Fe^{3+}$ salts: e.g. orthophosphate, pyrophosphate, (other anions possible) Oxygen (††) on platinum, gold or other catalytic surfaces |
| Intercalation compounds | Graphite with Li, K, Ca, Na, Mg | Vanadium oxide Manganese oxide |

Thus, when the system 110 is in contact with the conducting fluid, a current path is formed through the conducting fluid between the dissimilar materials 263, 264. A control device 265 is secured to the framework 262 and electrically coupled to the materials 263, 264. The control device 265 includes electronic circuitry, for example control logic that is capable of controlling and altering the conductance between the materials 263, 264.

The voltage potential created between the dissimilar materials 263, 264 provides the power for operating the system as well as produces the current flow through the conducting fluid and the system 110. In one aspect, the system 110 operates in direct current mode. In an alternative aspect, the system 110 controls the direction of the current so that the direction of current is reversed in a cyclic manner, similar to alternating current. As the system reaches the conducting fluid or the electrolyte, where the fluid or electrolyte component is provided by a physiological fluid, e.g., stomach acid, the path for current flow between the dissimilar materials 263, 264 is completed external to the system 110; the current path through the system 110 is controlled by the control device 265. Completion of the current path allows for the current to flow and in turn a receiver, not shown, can detect the presence of the current and recognize that the system 110 has been activate and the desired event is occurring or has occurred.

In some embodiments, the two dissimilar materials 263, 264 are similar in function to the two electrodes needed for a direct current power source, such as a battery. The conducting liquid acts as the electrolyte needed to complete the power source. The completed power source described is defined by the physical chemical reaction between the dissimilar materials 263, 264 of the system 110 and the surrounding fluids of the body. The completed power source may be viewed as a power source that exploits reverse electrolysis in an ionic or a conduction solution such as gastric fluid, blood, or other bodily fluids and some tissues. Additionally, the environment may be something other than a body and the liquid may be any conducting liquid. For example, the conducting fluid may be salt water or a metallic based paint.

In certain aspects, the two dissimilar materials 263, 264 are shielded from the surrounding environment by an additional layer of material. Accordingly, when the shield is dissolved and the two dissimilar materials 263, 264 are exposed to the target site, a voltage potential is generated.

In certain aspects, the complete power source or supply is one that is made up of active electrode materials, electrolytes, and inactive materials, such as current collectors, packaging. The active materials are any pair of materials with different electrochemical potentials. Suitable materials are not restricted to metals, and in certain embodiments the paired materials are chosen from metals and non-metals, e.g., a pair made up of a metal (such as Mg) and a salt (such as CuI). With respect to the active electrode materials, any pairing of substances—metals, salts, or intercalation compounds—with suitably different electrochemical potentials (voltage) and low interfacial resistance are suitable.

A variety of different materials may be employed as the materials that form the electrodes. In certain embodiments, electrode materials are chosen to provide for a voltage upon contact with the target physiological site, e.g., the stomach, sufficient to drive the system of the identifier. In certain embodiments, the voltage provided by the electrode materials upon contact of the metals of the power source with the target physiological site is 0.001 V or higher, including 0.01 V or higher, such as 0.1 V or higher, e.g., 0.3 V or higher, including 0.5 volts or higher, and including 1.0 volts or higher, where in certain embodiments, the voltage ranges from about 0.001 to about 10 volts, such as from about 0.01 to about 10 V.

Referring still to FIG. 4, the dissimilar materials 263, 264 provide the voltage potential to activate the control device 265. Once the control device 265 is activated or powered up, the control device 265 can alter conductance between the first and second materials 263, 264 in a unique manner. By altering the conductance between the first and second materials 263, 264, the control device 265 is capable of controlling the magnitude of the current through the conducting liquid that surrounds the system 110. This produces a unique current signature that can be detected and measured by a receiver (not shown), which can be positioned internal or external to the body. The receiver is disclosed in greater detail in U.S. patent application Ser. No. 12/673,326 entitled "BODY-ASSOCIATED RECEIVER AND METHOD" filed on Dec. 15, 2009, and published as 2010-0312188 A1 dated Dec. 9, 2010 which is incorporated herein by reference in its entirety. In addition to controlling the magnitude of the current path between the materials, non-conducting materials, membrane, or "skirt" are used to increase the "length" of the current path and, hence, act to boost the conductance path, as disclosed in the U.S. patent application Ser. No. 12/238,345 entitled, "IN-BODY DEVICE WITH VIRTUAL DIPOLE SIGNAL AMPLIFICATION" filed Sep. 25, 2008, the entire content of which is incorporated herein by reference. Alternatively, throughout the disclosure herein, the terms "non-conducting material," "membrane," and "skirt" are interchangeably used with the term "current path extender" without impacting the scope or the present embodiments and the claims herein. The skirt, shown in portion at 266, 267, respectively, may be associated with, e.g., secured to, the framework 262. Various shapes and configurations for the skirt are contemplated as within the scope of the various aspects of the present disclosure. For example, the system 110 may be surrounded entirely or partially by the skirt and the skirt may be positioned along a central axis of the system 120 or off-center relative to a central axis. Thus, the scope of the present disclosure as claimed herein is not limited by the shape or size of the skirt. Furthermore, in other embodiments, the dissimilar materials 263, 264 may be separated by one skirt that is positioned in any defined region between the dissimilar materials 263, 264.

The system 110 may be grounded through a ground contact. The system 110 also may include a sensor module. In operation, ion or current paths are established between the first material 263 to the second material 264 and through a conducting fluid in contact with the system 110. The voltage potential created between the first and second materials 263, 264 is created through chemical reactions between the first and second materials 263, 264 and the conducting fluid. In one aspect, the surface of the first material 263 is not planar, but rather an irregular surface. The irregular surface increases the surface area of the material and, hence, the area that comes in contact with the conducting fluid.

In one aspect, at the surface of the first material 263, there is chemical reaction between the material 263 and the surrounding conducting fluid such that mass is released into the conducting fluid. The term mass as used herein refers to protons and neutrons that form a substance. One example includes the instant where the material is CuCl and when in contact with the conducting fluid, CuCl becomes Cu (solid) and Cl— in solution. The flow of ions into the conduction fluid is via ion paths. In a similar manner, there is a chemical reaction between the second material 264 and the surrounding conducting fluid and ions are captured by the second material 264. The release of ions at the first material 263 and capture of ion by the second material 264 is collectively referred to as the ionic exchange. The rate of ionic exchange and, hence the ionic emission rate or flow, is controlled by the control device 265. The control device 265 can increase or decrease the rate of ion flow by altering the conductance, which alters the impedance, between the first and second materials 263, 264. Through controlling the ion exchange, the system 110 can encode information in the ionic exchange process. Thus, the system 110 uses ionic emission to encode information in the ionic exchange.

The control device 265 can vary the duration of a fixed ionic exchange rate or current flow magnitude while keeping the rate or magnitude near constant, similar to when the frequency is modulated and the amplitude is constant. Also, the control device 265 can vary the level of the ionic exchange rate or the magnitude of the current flow while keeping the duration near constant. Thus, using various combinations of changes in duration and altering the rate or magnitude, the control device 265 encodes information in the current flow or the ionic exchange. For example, the control device 265 may use, but is not limited to any of the following techniques namely, Binary Phase-Shift Keying (PSK), Frequency Modulation (FM), Amplitude Modulation (AM), On-Off Keying, and PSK with On-Off Keying.

Various aspects of the system 110 may comprise electronic components as part of the control device 265. Components that may be present include but are not limited to: logic and/or memory elements, an integrated circuit, an inductor, a resistor, and sensors for measuring various parameters. Each component may be secured to the framework and/or to another component. The components on the surface of the support may be laid out in any convenient configuration. Where two or more components are present on the surface of the solid support, interconnects may be provided.

The system 110 controls the conductance between the dissimilar materials and, hence, the rate of ionic exchange or the current flow. Through altering the conductance in a specific manner the system is capable of encoding information in the ionic exchange and the current signature. The ionic exchange or the current signature is used to uniquely identify the specific system. Additionally, the system 110 is capable of producing various different unique exchanges or signatures and, thus, provides additional information. For example, a second current signature based on a second conductance alteration pattern may be used to provide additional information, which information may be related to the physical environment. To further illustrate, a first current signature may be a very low current state that maintains an oscillator on the chip and a second current signature may be a current state at least a factor of ten higher than the current state associated with the first current signature.

Figure 5:
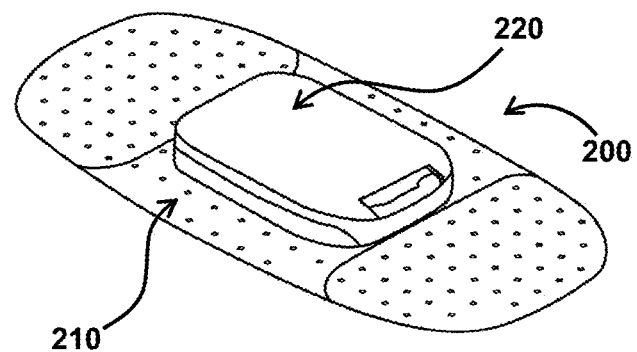
FIG. 5 shows a view of a re-wearable physiological monitoring device according to at least one aspect of the present disclosure with the reusable component and the disposable component latched together.

FIG. 5 shows a view of the re-wearable physiological monitoring device 200 of the present disclosure fully assembled. As shown, the re-wearable physiological monitoring device 200 comprises two parts—a disposable component 210 and a reusable component 220. The reusable component preferably has a similar footprint to the cradle of the disposable component and latches on top of the disposable component as shown. The disposable component 210 and the reusable component 220 may be latched together or unlatched by the user as needed.

In an aspect of the present disclosure, the electrodes, the adhesive patch, and the battery are both located in the disposable component 210. Since the adhesive patch of the re-wearable physiological monitoring device needs to be changed at regular intervals, and since a user would need to change or re-charge the battery at regular intervals as well, placing the adhesive patch and the battery in the same disposable component makes battery changes automatic for the user, saving the user from an additional maintenance task. The battery preferably has a useful life of approximately the same time period as the adhesive to avoid waste; in an aspect of the present disclosure, the expected life of the disposable component is approximately 10-14 days, but the present disclosure is not limited to this particular time period. In an aspect, the battery is a LiMn coin cell, but any other disposable battery is suitable for practicing the present disclosure.

This configuration of the re-wearable physiological monitoring device permits easy user replacement of consumable components such as adhesive patches or batteries, while avoiding waste of durable components such as electronics. This permits the durable high-cost electronic components to only be purchased once by a user, lowering the overall cost of use for the system.

One problem created by this configuration is that the reusable component may be left without power whenever a user disconnects it from the disposable component. To address this problem, in one aspect, the reusable component may comprise a clock or some other electronic component that needs to be kept continuously active. For example, a device that needs to track the exact timing of particular events needs to keep a continuously running clock. In an aspect of the present disclosure, the reusable component comprises a supercapacitor 219 (shown in FIG. 2) connected to any such components, wherein the supercapacitor is charged by the battery during normal use. The supercapacitor 219 is preferably connected only to the components that need to be kept powered on, such as a clock, to reduce power usage. In an embodiment, however, the supercapacitor is connected to the same connections as the battery and powers all the electronic components of the reusable component. In an aspect of the invention, the supercapacitor has a capacitance that permits it to provide power to the components that require it for a maximum of 3 days. It will be understood, however, that any other capacitance of the supercapacitor 219 and any other duration of power supply is included in the present disclosure.

Figure 6:
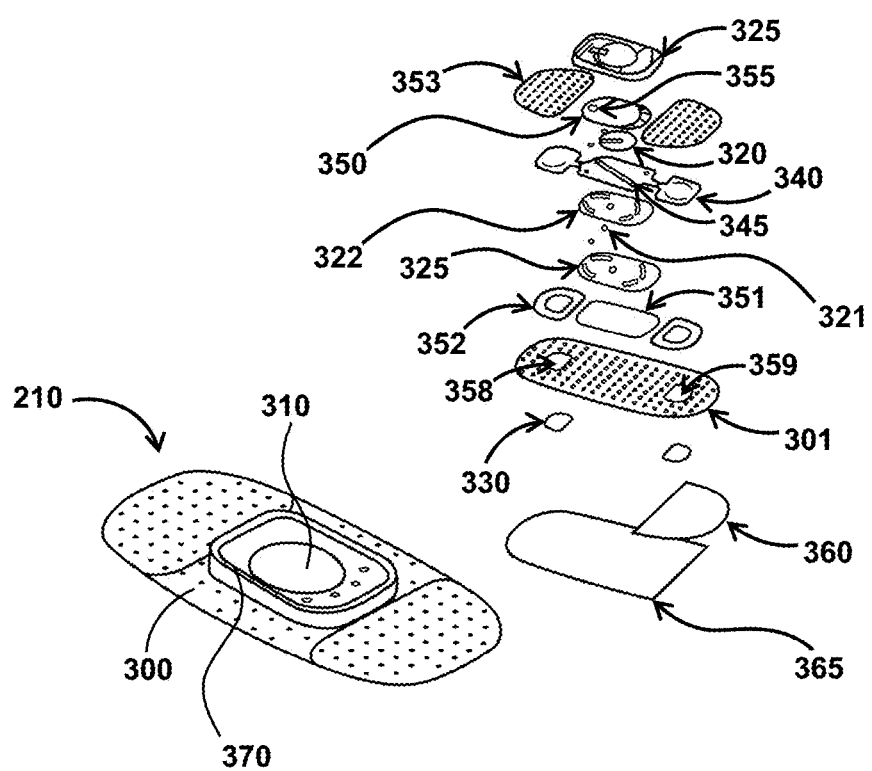
FIG. 6 shows two views of a disposable component according to at least one aspect of the present disclosure.

FIG. 6 shows a view of one aspect of the disposable component 210 fully assembled and an exploded view of the disposable component 210 showing its components. As shown, the disposable component 210 comprises an adhesive patch 300 and a cradle 310 disposed on top of the adhesive patch 300. The cradle 310 comprises a battery 320 located within its housing 325.

The adhesive patch 300 comprises multiple parts as shown on the exploded view in FIG. 3. The skin adhesive 301 preferably comprises a large enough footprint to avoid user discomfort. According to at least one aspect of the invention, a border with a thickness of at least 0.5 cm, and preferably 1 cm, of free adhesive (i.e., without any components mounted thereon) should be available all around the perimeter of the skin adhesive to avoid user discomfort.

Figure 11:
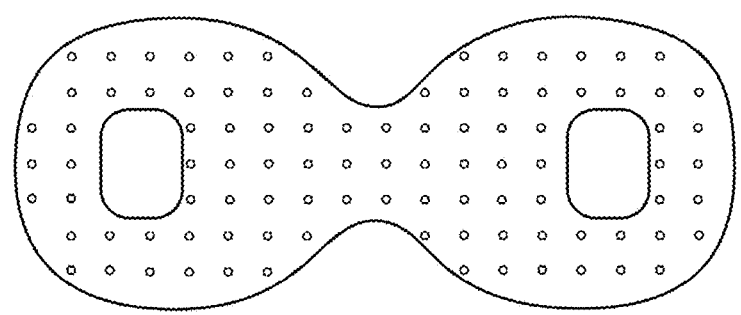
FIG. 11 shows a view of the adhesive patch of the re-wearable physiological monitoring device according to at least one aspect of the present disclosure.

While in the aspect shown in FIG. 6, the adhesive patch 300 has a "racetrack" shape, other shapes may also be used. In an alternate embodiment, the adhesive patch 300 has a "dog-bone" shape as shown in FIG. 11, with a narrow section in the middle and widened sections closer to the ends. This enables the electrodes to adhere well to the skin while avoiding unnecessary adhesive material in the middle of the patch and makes the patch more flexible to improve comfort.

In some aspects, it may be desirable for the adhesive patch to be stretchable bidirectionally so that it can stretch with the skin. Adhesive materials that are stretchable only unidirectionally, or not stretchable at all, may not conform to the user's skin sufficiently to allow for comfort, since human skin is stretchable bidirectionally. This may lead to discomfort and detachment of the adhesive patch. A bidirectionally stretchable adhesive patch greatly improves user comfort and patch adherence.

As shown in the Figure, skin adhesive 301 comprises two openings 358 and 359 through which hydrogel patches 330 are inserted. The hydrogel patches 330 are used to connect the user's skin to electrodes 340 for conductive signals to be conveyed from the user's skin to the re-wearable physiological monitoring device. These conductive signals may come from the user's own body (such as cardiac signals) or may be generated by an ingestible event marker (IEM) ingested by the user. The hydrogel patches may or may not comprise adhesives; in an aspect, the hydrogel patches do not comprise any additional adhesive, since hydrogel itself is mildly adhesive, which is sufficient for the adhesion required by the present disclosure.

Backing layers 360 and 365 are provided to protect the adhesive until it is adhered to the user's skin. In an aspect of the present disclosure, as shown in the Figure, the two backing layers slightly overlap with each other, and are larger than the footprint of the adhesive patch 300 to enable a user to peel them off more easily.

The electrodes 340 are preferably printed on a flexible circuit substrate along with any other electric connections required for the connection of the electrodes and the battery to the reusable component. The battery and electrode connections are routed to contacts 345 as shown; the battery 320 is connected to the flexible circuit substrate by means of rivets 321 through the flexible circuit tie layer 322. The contacts 345 will be discussed in greater detail hereinbelow.

Cradle adhesive 351 attaches cradle housing 325 to the skin adhesive patch 301. Hydrogel patches 330 are located in openings 358 and 359 of the skin adhesive patch 301 to connect electrodes 340 to the user's skin. Since hydrogel tends to expand upon exposure to moisture, it tends to lift the electrode adhesive from the patch; to prevent this occurrence, the width of the electrode adhesive surrounding the hydrogel has to be a minimum of 4.5 mm.

In an embodiment, cradle adhesive 351 is not present and only electrode adhesive 352 is used. This improves comfort for the user, since the cradle housing 325 is rigid and cannot stretch with the skin. A cover layer 353 is used to cover up the flexible circuit on top of the patch.

Gasket 350 is provided to protect the electronic components from water and dust. The gasket 350 will be discussed in greater detail hereinbelow.

Battery disconnect switch 355 is disposed on the gasket 350. The function of the battery disconnect switch 355 is to disconnect the battery from one of the connectors when a reusable component is not latched on to the disposable component. The battery disconnect switch will be discussed in greater detail hereinbelow.

FIG. 7 shows two views of the reusable component 220 of the physiological monitoring device of the present disclosure—a view of the reusable component fully assembled and an exploded view showing its components. Circuit board 400 is encased in a plastic housing comprising a bottom part 410 and a top part 420. The circuit board 400 comprises four spring loaded electrical connectors (e.g. pogo pin connectors) 430 that are used to connect the reusable component to the disposable component; two of the pogo pin connectors are used to connect to the battery 320 and two are used to connect to the electrodes 340. It will be understood that any number of pogo pin connectors is acceptable for practicing the present disclosure. Gasket 440 is placed in such a way as to form a waterproof enclosure around each pogo pin connector 430. The gasket will be discussed in greater detail hereinbelow.

The circuit board 400 may contain any components necessary for the proper functioning of the re-wearable physiological monitoring device. Such components may include processor and memory components, sensors, wireless transmitters and receivers, and so on; a block diagram of an aspect of the reusable component is shown in FIG. 2. The present disclosure, however, is not limited to any particular configuration of circuit board or any particular function of the reusable component of the re-wearable physiological monitoring device.

Ultrasonic Welding

As shown in FIG. 7, the plastic housing of the reusable component of the present disclosure comprises a bottom part 410 and a top part 420. The bottom part 410 and top part 420 are ultrasonically welded together, since this results in a strong and watertight connection.

One problem that frequently arises in ultrasonic welding of plastic housings containing PCBA's is that the ultrasonic vibrations are transmitted to the PCBA, damaging the components thereon. Since a typical PCBA is rigidly attached to the plastic housing during assembly prior to welding, such rigid attachment tends to transmit ultrasonic vibration to the PCBA. Such vibration may cause failure to components mounted to or otherwise coupled to the PCBA. This may be especially damaging for components such as accelerometers, which are utilized in many wearable physiological monitoring devices.

The present disclosure, in some embodiments, solves this problem by not attaching the PCBA rigidly to the plastic housing during assembly. During assembly, the PCBA 400 is loosely placed on the bottom part of the plastic housing 410, along with gasket 440. The top part of the plastic housing 420 is then placed on top of the bottom part of the plastic housing 410 and the PCBA 400, and the ultrasonic weld is performed around the perimeter of the plastic housing to attach the bottom part of the plastic housing 410 to the top part of the plastic housing 420. This results in a secure connection between the two parts of the plastic housing and an undamaged PCBA. In some embodiments, the tolerances between the top and bottom part of the plastic housing are tight enough that the PCBA is constrained when the ultrasonic welding process is finished. This keeps the PCBA in place and prevents rattling while still preventing damage to the PCBA during ultrasonic welding that would occur if PCBA was mounted to or otherwise coupled to the plastic housing.

Figure 12:
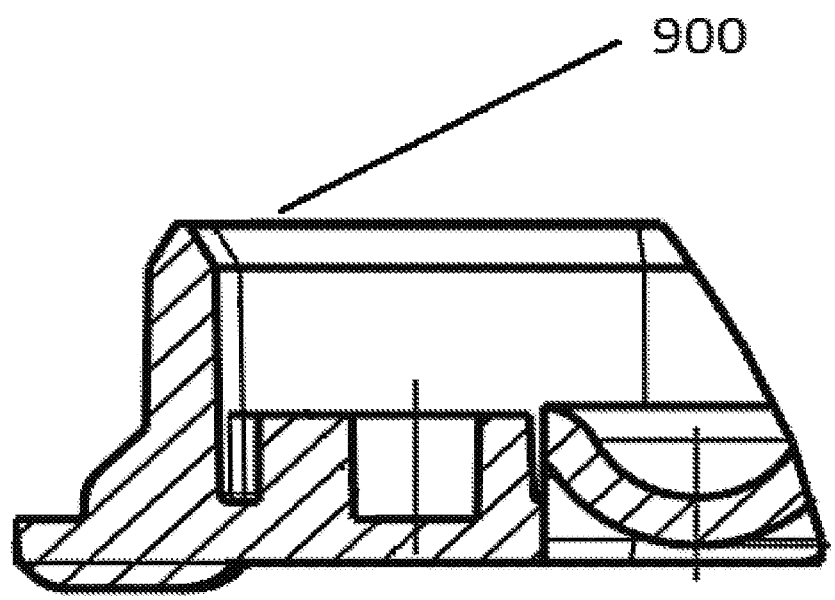
FIG. 12 shows a view of a wall feature on the bottom half of the plastic housing of the reusable component according to at least one aspect of the present disclosure.
Figure 13:
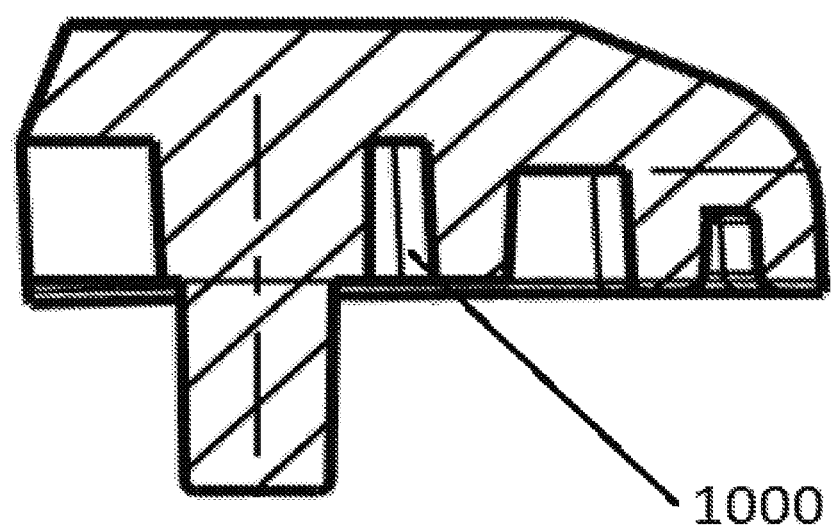
FIG. 13 shows a view of a wall feature on the top half of the plastic housing of the reusable component according to at least one aspect of the present disclosure.
Figure 14:
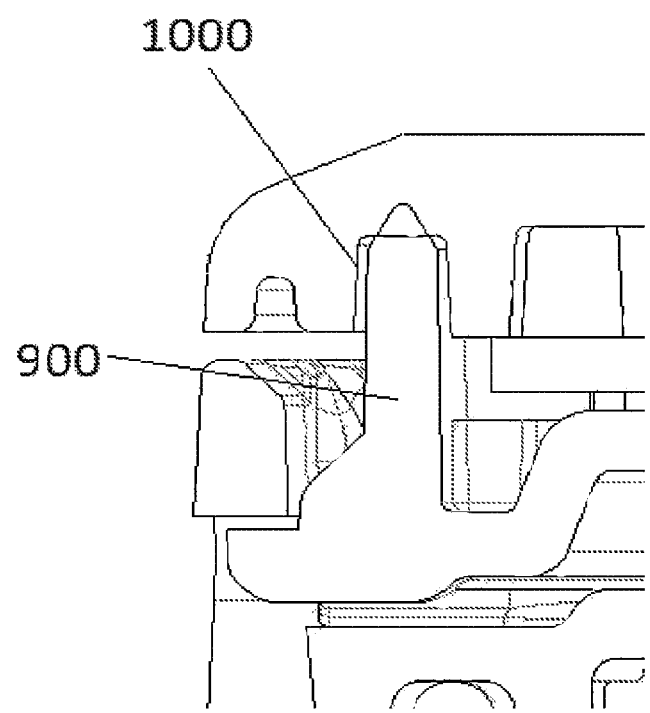
FIG. 14 shows a view of the wall features on the top half and the bottom half of the plastic housing of the reusable component according to at least one aspect of the present disclosure, assembled together.

In an aspect of the present disclosure, the bottom part of the plastic housing comprises a first wall feature that engages with a mating second wall feature on the top part of the plastic housing. This facilitates a secure connection between the two parts of the plastic housing during ultrasonic welding and ensures they remain aligned. FIG. 12 shows the first wall feature 900, in cross-section, on the bottom part of the plastic housing 410. The first wall feature 900 preferably is located near the edge to facilitate ultrasonic welding and to enable a secure connection around the edge. FIG. 13 shows the second wall feature 1000, in cross-section, on the top part of the plastic housing 420. The first wall feature 900 fits into the second wall feature 1000 during assembly and then melts together with the second wall feature 1000 during ultrasonic welding, resulting in a secure and waterproof connection. FIG. 14 shows the first wall feature 900 and the second wall feature 1000 mating together in an assembled plastic housing. As shown, the first wall feature 900 has a slight overlap with the second wall feature 1000, which melts together during ultrasonic welding. In an aspect, both first wall feature 900 and second wall feature 1000 continue all around the perimeter of, respectively, the bottom part of the plastic housing 410 and the top part of the plastic housing 420; however, the invention is not limited to that particular embodiment, as the wall features may only continue part of the way around the perimeter or may be located in only one part of the perimeter of the plastic housing.

In an aspect of the present disclosure, the watertightness of the connection between the bottom part of the plastic housing and the top part of the plastic housing is evaluated by observing the slight bulge that forms on the underside of the reusable component due to a small volume of air trapped between the top part of the plastic housing and the bottom part of the plastic housing. When the air is trapped during the weld, the internal volume of the reusable component is reduced as the weld melts the two parts of the housing together, while the internal pressure increases relative to atmospheric pressure. The physical change is elastic and non-destructive, and is transient, since the air eventually escapes from the reusable component; the gasket is gas permeable and results in a very slow leak. However, the "belly" bulge that occurs right after welding is a useful way to determine that a seal is formed that will resist water ingress. In an aspect of the present disclosure, the thickness of the reusable component is measured immediately after welding; if it is thinner than a predetermined value, the weld is assumed to be inadequately waterproof.

Battery Disconnect Switch

Figure 8:
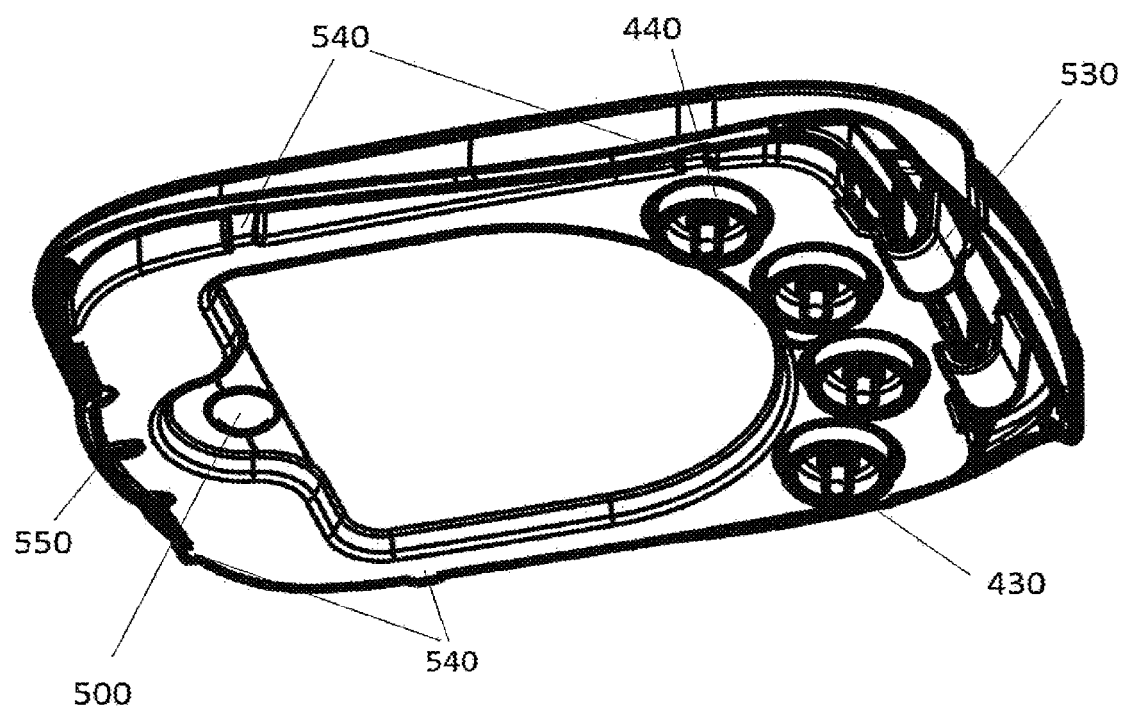
FIG. 8 shows a view of a reusable component according to at least one aspect of the present disclosure.
Figure 16:
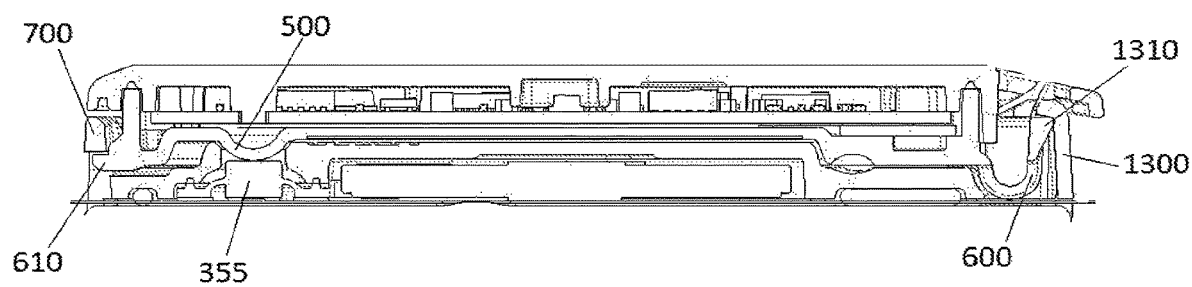
FIG. 16 shows a cross-sectional view of the reusable component and the disposable component assembled together according to at least one aspect of the present disclosure.

As shown in FIG. 6, kill switch 355 is located in the disposable component. It is preferably a pushbutton (pill keypad) as shown in the Figure, but may also be a dome switch or any other switch that is activated by pressure. The battery disconnect switch 355 disconnects the battery 320 from at least one connector 345 when the reusable component is not latched onto the disposable component. This prevents live electrical connections from being present when the reusable component is not in place, saves battery life, and allows a user to shower or perform other activities involving water while the reusable component is disconnected without fear of an electric shock or battery damage. As shown in FIG. 8, the reusable component comprises a protrusion 500 configured to press the pushbutton of the battery disconnect switch 355 when the reusable component engages with the disposable component. FIG. 16 shows a cross-sectional view of the protrusion 500 pressing on the pushbutton 355 when the reusable component is latched onto the disposable component. In an aspect, the battery disconnect switch 355 does not engage until the reusable component is fully latched onto the disposable component. The protrusion 500 is preferably molded into the plastic housing of the reusable component, but may be manufactured separately and attached adhesively to the housing. The protrusion 500 may be rigid or slightly elastic.

In an aspect of the invention, the pushbutton of the battery disconnect switch comprises the following features. The bottom of the pushbutton 355 comprises a conductive plate. A trace coming from the battery 320 comprises an open circuit located under the bottom of the pushbutton. When the pushbutton is pushed down, the conductive plate comes down onto the trace and connects the two sides of the open circuit, connecting the battery to the rest of the circuit. The pushbutton is preferably spring-loaded so that when there is no downward force applied to it, it is raised, and the conductive plate is not in contact with the trace. The reusable component is configured so that when it is fully latched onto the disposable component, it pushes down the pushbutton so that the conductive plate connects the two sides of the open circuit. In an aspect of the invention, the reusable component comprises a protrusion 500 that pushes the pushbutton; however, in other aspects of the invention, the pushbutton may be configured so that the protrusion is not required. In those aspects of the invention, the bottom side of the reusable component (which may be flat or may comprise any other shape) pushes the pushbutton down when the reusable component is fully latched onto the disposable component.

Gaskets

In some embodiments, the present disclosure comprises a gasket to prevent any water damage to the re-wearable physiological monitoring device and to enable a user to wear the re-wearable physiological monitoring device for water-related activities such as showering or swimming.

One problem that may be encountered by a user when using the present disclosure is that if the reusable component is disconnected and then the disposable component encounters water (for example, the user takes off the reusable component and then takes a shower), water may still be present around the connectors between the reusable and disposable components when the reusable component is reconnected. This may result in a short circuit and damage the electronics of the reusable component.

To prevent this problem, gasket 440 is provided. The gasket 440 comprises an enclosure around each individual pogo pin 430, as shown in FIG. 8. Each enclosure provides a hermetic seal to the cradle housing 325 shown in FIG. 6. This means that even if water is present on the cradle or the reusable component when the reusable component is latched onto the disposable component, the gasket 440 isolates each pogo pin and prevents any water from forming an unwanted short circuit between any two pogo pins. The gasket 440 is preferably made of silicone rubber, but any other elastic waterproof material may also be used for practicing the present disclosure. In an aspect, the enclosures around each pogo pin are cylindrical and approximately 5 mm in diameter; other shapes of enclosures and other dimensions may also be used for practicing the present disclosure, as long as each enclosure encloses only one electrical contact in a waterproof manner.

While gasket 440 may be contained within the reusable component, it is also possible for the gasket to be contained within the disposable component, or for part of the gasket to be contained within the reusable component and part within the disposable component, as long as a waterproof enclosure is formed around each connector when the reusable component is latched to the disposable component.

Latching Features

Since the present disclosure is a physiological monitoring device, it may be used by people who have cognitive problems or motor-control problems, either one of which may make it very difficult for them to latch and unlatch the reusable component from the disposable component. For example, a latching system that requires one particular angle of approach (i.e. a "garage door" style latch where a user has to hook one end of the reusable component into the disposable component and then snap it down) may be too difficult for some users to manipulate correctly due to cognitive and/or motor-control problems. The present disclosure, in multiple embodiments, comprises various features to enable easy latching and unlatching.

In some embodiments of the present disclosure, the reusable component 210 comprises an asymmetrical wall feature 450 (shown in FIG. 7). The disposable component 220 comprises an asymmetrical cradle feature 370 (shown in FIG. 6) whose contours match the asymmetrical wall feature when the reusable component is placed on the disposable component in the correct orientation. Since the wall feature and cradle feature are both asymmetrical, they will not allow the reusable component to be latched onto the disposable component if its orientation is incorrect. In an aspect of the present disclosure, a curved "swoosh" contour is used for the asymmetrical wall feature and the asymmetrical cradle feature, but any other shape may be used, as long as it is asymmetrical and allows the two components to fit together only in one orientation.

Figure 9:
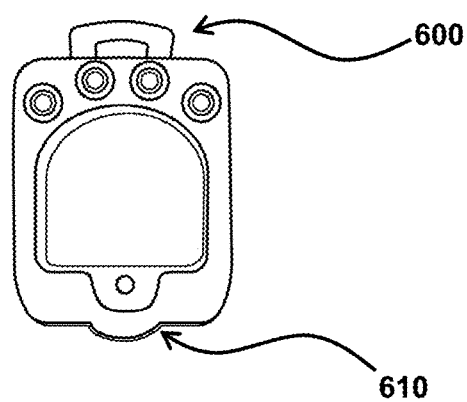
FIG. 9 shows a bottom view of a reusable component according to at least one aspect of the present disclosure.
Figure 10:
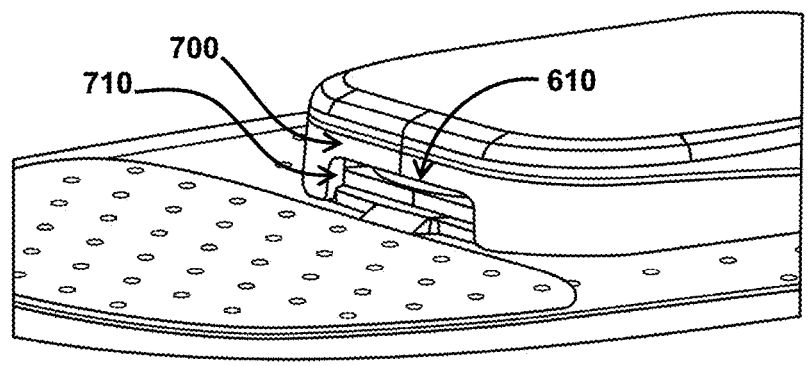
FIG. 10 shows a view of the rear latch of the re-wearable physiological monitoring device according to at least one aspect of the present disclosure.

In some embodiments of the present disclosure, as shown in FIG. 9, the reusable component comprises a front snap feature 600 and a rear snap feature 610. In this embodiment, the front snap feature 600 is a flexible beam that engages with a latch on the cradle. The rear snap feature 610 is a rigid protrusion. As shown in FIG. 10, the cradle comprises a flexible horizontal beam 700 that can flex sufficiently to allow the rear snap feature 610 to pass by it and then flex back to engage the protrusion of the rear snap feature to hold the reusable component in place. A slot 710 is cut in the cradle to allow the protrusion of the rear snap feature to engage the horizontal beam 700.

As shown in FIG. 7, the reusable component may also include a bridge feature 1400 to protect the front snap feature and to prevent it from accidentally detaching if the front snap feature is accidentally depressed. The bridge feature preferably protrudes as far as, or slightly beyond, the front snap feature and is rigid enough to not move the front snap feature if the bridge feature is pressed.

FIG. 16 shows a cross-sectional view of the front snap feature and the rear snap feature. As shown in the Figure, the front snap feature 600 engages with a latch 1300 on the cradle to hold it in place. The rear snap feature 610 engages with a slot cut in the flexible horizontal beam 700 as shown. As shown in the Figure, the flexible horizontal beam 700 is slightly chamfered to allow it to deflect out of the way when the rear snap feature 610 passes by it; the rear snap feature 610 is also slightly chamfered to improve deflection. As shown, the front snap feature 600 is a flexible beam that is U-shaped to allow it to deflect, comprising a protrusion 1310 that engages with the latch 1300 on the cradle. The protrusion 1310 has a slanted surface that allows the front snap feature 600 to deflect while the reusable component is pushed down onto the disposable component, and a horizontal surface that engages with the latch 1300 when the reusable component is fully engaged with the disposable component.

The front snap feature and rear snap feature enable flexibility in how the reusable component is inserted into the cradle of the disposable component. It may be inserted in a "garage door" style motion where the rear snap feature is inserted into the corresponding slot on the cradle and then the reusable component is swung down until the front snap feature latches into the cradle. The reusable component may also simply be pushed straight down so that both the front snap feature and the rear snap feature engage at the same time. Also, the front snap feature may be engaged first and then the reusable component may be swung down to latch the rear snap feature in place. This enables users with cognitive and/or motor problems to still be able to attach the reusable component to the disposable component.

It will be understood that any type of snap fastening connection may be used for the front snap feature and rear snap feature and that the present disclosure is not limited to the particular embodiment described.

Figure 15:
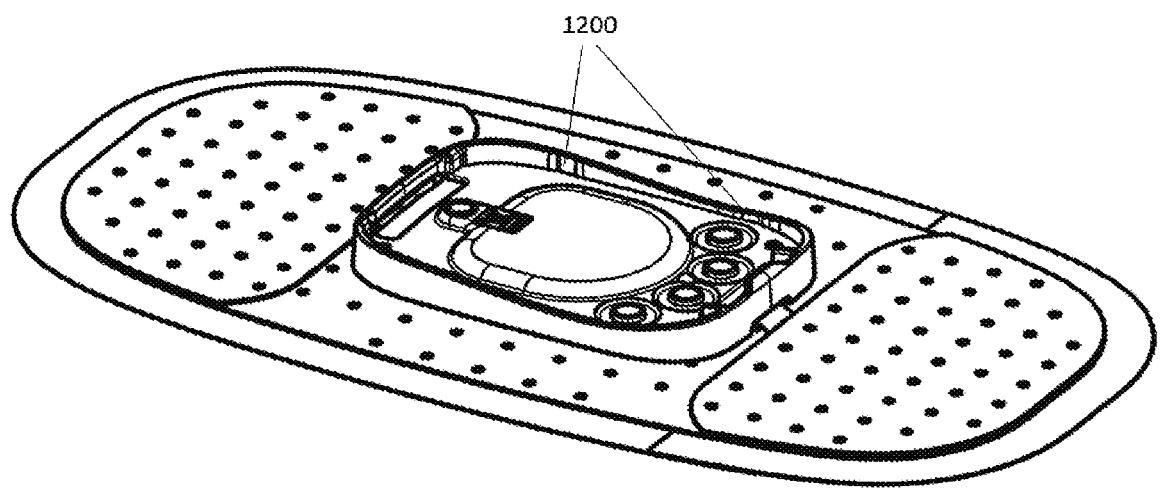
FIG. 15 shows a view of the cutouts on the disposable component according to at least one aspect of the present disclosure.

In some embodiments of the present disclosure, alignment feet 540 are provided around the perimeter of the reusable component for alignment of the reusable component to the cradle of the disposable component. The alignment feet 540 are spaced at regular intervals around the perimeter of the reusable component; in an aspect, 6 alignment feet are provided. The alignment feet 540 fit into corresponding cutouts 1200 on the disposable component, shown in FIG. 15. This helps align the reusable component to the disposable component during latching.

In an embodiment, the bottom-most portion of the alignment feet 540 is slightly rounded or chamfered to facilitate entry into the cutouts 1200.

Electrical Contacts

In some embodiments of the present disclosure, the electrical connections between the reusable component and the disposable component are made by pogo pins 430 (shown in FIG. 7) that connect to printed electrical contacts 345 (shown in FIG. 6). It will be understood that pogo pins refer to connectors that employ spring loaded pins to allow for some range of travel while maintaining electrical contact with components. However, typical pogo pins often include sharp ended pins that may, over time, cause damage to the contacts, depending on the materials used for the contact. In particular, where pogo pins contact an electrical conduct made from a single conductive ink that is printed onto a flexible circuit, it has been found that in the course of use the pogo pins may scrape or scratch away the conductive ink such that electrical connection is not reliable. To avoid this issue, contacts 345 are printed using two layers of conductive ink with different physical and electrical properties. In particular, the first layer of ink may have increased conductivity relative to the second layer of ink. And, the second layer of ink, which is printed on top of the first layer, may be made from a material with smaller particle sizes relative to the first layer of ink. The increased conductivity of the first layer ensures that there is adequate conductivity for a reliable electrical connection and the reduced particle size of the second layer ensures that the layer is not entirely scraped away, but rather that the particles are able to fill into any voids created by scratches or scraping by the pogo pins. Although any suitable materials may be used, in some embodiments the contact may include a first layer of ink comprising large metal flakes, and a second layer of ink printed on top of the first layer, the second layer comprising carbon ink. While carbon ink is not as conductive as metal ink, if metal ink is used by itself, the tips of the pogo pins tend to scratch away the ink during normal use, resulting in failed connections as described above. Using a carbon ink on top of the metal ink enables smaller carbon particles to act as a lubricant and to fill in voids created by any scratches made by the pogo pins and maintain the electrical connection.

In an aspect, the metal ink is silver ink comprising silver flakes of approximately 5-7 μm in size, and the carbon ink comprises carbon particles of approximately 1 μm in size. Other metal-based inks comprising metals such as copper, or inks comprising different sizes of metal particles ranging from nanoparticles to large 10-micron scale flakes, may also be used; graphene-based inks, carbon nanotubes, and carbon particles may also be used for the carbon ink component. The layer of silver ink is preferably 0.01±0.0051 mm thick, while the layer of carbon ink is preferably 0.013±0.0051 mm thick.

While various details have been set forth in the foregoing description, it will be appreciated that the various aspects of the re-wearable physiological monitoring device may be practiced without these specific details. For example, for conciseness and clarity selected aspects have been shown in block diagram form rather than in detail. Some portions of the detailed descriptions provided herein may be presented in terms of instructions that operate on data that is stored in a computer memory. Such descriptions and representations are used by those skilled in the art to describe and convey the substance of their work to others skilled in the art. In general, an algorithm refers to a self-consistent sequence of steps leading to a desired result, where a "step" refers to a manipulation of physical quantities which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities.

Unless specifically stated otherwise as apparent from the foregoing discussion, it is appreciated that, throughout the foregoing description, discussions using terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

It is worthy to note that any reference to "one aspect," "an aspect," "one embodiment," or "an embodiment" means that a particular feature, structure, or characteristic described in connection with the aspect is included in at least one aspect. Thus, appearances of the phrases "in one aspect," "in an aspect," "in some embodiments," or "in an embodiment" in various places throughout the specification are not necessarily all referring to the same aspect. Furthermore, the particular features, structures or characteristics may be combined in any suitable manner in one or more aspects.

Although various embodiments have been described herein, many modifications, variations, substitutions, changes, and equivalents to those embodiments may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed embodiments. The following claims are intended to cover all such modification and variations.

Some or all of the embodiments described herein may generally comprise technologies for various aspects of re-wearable physiological monitoring devices, or otherwise according to technologies described herein. In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In some embodiments, several portions of the subject matter described herein may be implemented via Application Specific Integrated Circuits (ASICs), Field Programmable Gate Arrays (FPGAs), digital signal processors (DSPs), or other integrated formats. Those skilled in the art will recognize, however, that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

U.S. Provisional Patent Application No. 62/685,855, titled MONITORING A SENSOR ASSEMBLY FOR REPLACEMENT STRIP, filed Jun. 15, 2018; International Application No. PCT/US2019/037257, titled MONITORING A SENSOR ASSEMBLY FOR REPLACEMENT STRIP, filed Jun. 14, 2019; U.S. Provisional Patent Application No. 62/685,878, titled LOW POWER RECEIVER FOR IN VIVO CHANNEL SENSING AND INGESTIBLE SENSOR DETECTION WITH WANDERING FREQUENCY, filed Jun. 15, 2018; International Application No. PCT/US2019/037307, titled LOW POWER RECEIVER FOR IN VIVO CHANNEL SENSING AND INGESTIBLE SENSOR DETECTION WITH WANDERING FREQUENCY, filed Jun. 14, 2019, are each hereby Incorporated herein by reference in their entireties.

All of the above-mentioned U.S. patents, U.S. patent application publications, U.S. patent applications, foreign patents, foreign patent applications, non-patent publications referred to in this specification and/or listed in any Application Data Sheet, or any other disclosure material are incorporated herein by reference, to the extent not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken as limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

Some aspects may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory. Further, implementation of at least part of a system for performing a method in one territory does not preclude use of the system in another territory.

Although various embodiments have been described herein, many modifications, variations, substitutions, changes, and equivalents to those embodiments may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed embodiments. The following claims are intended to cover all such modification and variations.

In summary, numerous benefits have been described which result from employing the concepts described herein. The foregoing description of the one or more embodiments has been presented for purposes of illustration and description. It is not intended to be exhaustive or limiting to the precise form disclosed. Modifications or variations are possible in light of the above teachings. The one or more embodiments were chosen and described in order to illustrate principles and practical application to thereby enable one of ordinary skill in the art to utilize the various embodiments and with various modifications as are suited to the particular use contemplated. It is intended that the claims submitted herewith define the overall scope.

The invention claimed is:

1. A wearable physiological monitoring device, comprising:
   a disposable component comprising:
      a first electrode;
      a second electrode;
      a cradle, comprising:
         a battery;
         a first electrical contact and a second electrical contact, both the first and second electrical contacts being electrically coupled to the battery;
         a third electrical contact electrically coupled to the first electrode;
         a fourth electrical contact electrically coupled to the second electrode;
         a battery disconnect switch located between the first electrical contact and the battery, said battery disconnect switch comprising:
            a first trace electrically coupled to the first electrical contact, said first trace comprising a first free end;
            a second trace electrically coupled to the battery, said second trace comprising a second free end, wherein the first free end is electrically isolated from the second free end;
            a button comprising a top side in proximity to the first trace and a bottom side in proximity to the second trace; and
            a conductive plate located on the bottom side of the button; and
   a reusable component configured to be secured to the disposable component, the reusable component comprising:
      an electronics module; and
      an electrical interface associated with the electronics module and configured to interface with at least one of the first, second, third, and fourth electrical contacts of the disposable component;
      wherein the battery is configured to connect to the reusable component by the conductive plate connecting to the first free end of the first trace and the second free end of the second trace when the button is pushed down onto the reusable component.

2. The device of claim 1 wherein the reusable component is configured to apply pressure to the button when the reusable component is connected to the disposable component.

3. The device of claim 1, wherein the reusable component comprises a protrusion configured to apply pressure to the button when the reusable component is connected to the disposable component.

4. The device of claim 1, wherein the disposable component further comprises a disposable component latching system; and the reusable component further comprises a reusable component latching system configured to operably engage the disposable component latching system.

5. The device of claim 1, wherein the electrical interface of the reusable component comprises a fifth electrical contact for electrically coupling the electronics module to the first electrical contact, a sixth electrical contact for electrically coupling the electronics module to the second electrical contact, a seventh electrical contact for electrically coupling the electronics module to the third electrical contact, and an eighth electrical contact for electrically coupling the electronics module to the fourth electrical contact.

6. The device of claim 5, further comprising:
a gasket, wherein the gasket comprises a first individual enclosure around the fifth electrical contact that does not enclose any other electrical contact, a second individual enclosure around the sixth electrical contact that does not enclose any other electrical contact, a third individual enclosure around the seventh electrical contact that does not enclose any other electrical contact, and a fourth individual enclosure around the eighth electrical contact that does not enclose any other electrical contact, in such a way that water cannot enter or exit any individual enclosures when the reusable component is engaged with the disposable component.

7. The device of claim 6, wherein the gasket comprises a top half attached to the reusable component and a bottom half attached to the disposable component.

8. The device of claim 6, wherein each one of the first, second, third, and fourth individual enclosure is cylindrical in shape.

9. The device of claim 1, wherein the button is spring-loaded so that in a first configuration, the conductive plate is not in electrical contact with the first free end and the second free end, and in a second configuration when pressure is applied to the button, the conductive plate comes into electrical contact with the first free end and the second free end so as to electrically couple the first free end to the second free end.

10. The device of claim 1, wherein the battery disconnect switch, the battery, the first trace, the second trace, and the reusable component are arranged in a stacked configuration.

* * * * *